United States Patent
Pflücker et al.

(10) Patent No.: US 7,264,795 B2
(45) Date of Patent: Sep. 4, 2007

(54) SUNSCREEN COMPOSITION

(75) Inventors: Frank Pflücker, Darmstadt (DE); Hans-Jürgen Driller, Gross-Umstadt (DE); Laure Vouzellaud, Montrouge (FR); Francois Marchio, Scarsdale, NY (US); Hervé Guinard, Nevilly sur Seine (FR); Ratan Chaudhuri, Lincoln Park, NY (US)

(73) Assignee: Merck Patent Gesellschaft, Darmstadt (DE)

(*) Notice: Subject to any disclaimer, the term of this patent is extended or adjusted under 35 U.S.C. 154(b) by 576 days.

(21) Appl. No.: 10/485,086

(22) PCT Filed: Jul. 18, 2002

(86) PCT No.: PCT/EP02/08011
§ 371 (c)(1), (2), (4) Date: Jan. 28, 2004

(87) PCT Pub. No.: WO03/011239
PCT Pub. Date: Feb. 13, 2003

(65) Prior Publication Data
US 2004/0175335 A1  Sep. 9, 2004

(30) Foreign Application Priority Data
Jul. 31, 2001  (EP) .................. 01117747

(51) Int. Cl.
A61Q 19/04   (2006.01)
A61Q 17/00   (2006.01)
A61K 8/02    (2006.01)
A61K 8/11    (2006.01)

(52) U.S. Cl. .............. 424/59; 424/60; 424/400; 424/401; 424/450

(58) Field of Classification Search ............ 424/59, 424/60, 400, 401
See application file for complete search history.

(56) References Cited

U.S. PATENT DOCUMENTS

| | | | |
|---|---|---|---|
| 6,159,453 A * | 12/2000 | Avnir et al. | 424/59 |
| 6,242,099 B1 | 6/2001 | Grandmontagne et al. | |
| 6,303,149 B1 | 10/2001 | Magdassi et al. | |
| 6,387,497 B1 | 5/2002 | Nishida et al. | |

FOREIGN PATENT DOCUMENTS

| | | |
|---|---|---|
| EP | 1041095 | 10/2000 |
| FR | 2799119 | 4/2001 |
| FR | 2799120 | 4/2001 |
| WO | WO 0009652 | 2/2000 |

OTHER PUBLICATIONS

Database WPI Week 199421 Derwent Publications Ltd., London, GB; An 1994-173649 XP002230487.

* cited by examiner

*Primary Examiner*—Shelley A. Dodson
(74) *Attorney, Agent, or Firm*—Millen, White, Zelano & Branigan, P.C.

(57) ABSTRACT

The present invention relates to a composition having UV protection properties, charaterized in that the formulation comprises at least one encapsulated organic sunscreen and does not penetrate the skin essentially.

20 Claims, 5 Drawing Sheets

Figure 2

Figure 1:
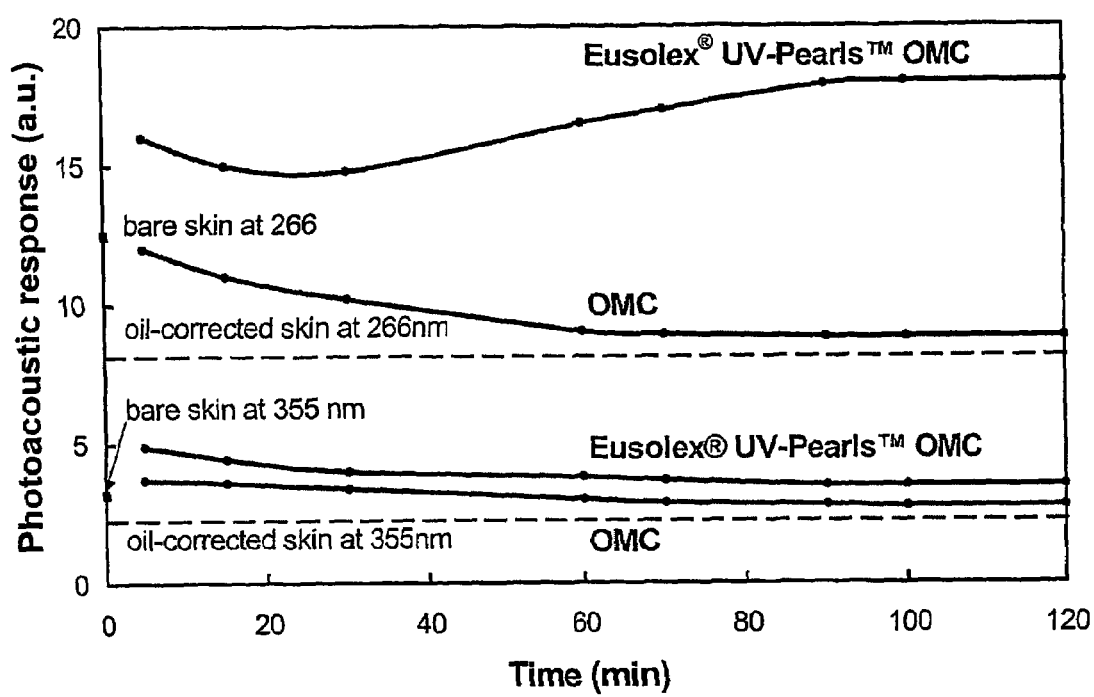

Stratum corneum (%) vs Concentration of OMC, encapsulated (µg/cm²)

SUNSCREEN COMPOSITION

The present invention relates to sunscreen compositions.

A suntan of the skin to whatever degree is regarded in today's society as attractive and as an expression of vigour and sportiness. As well as this desired effect of the sun on the skin, a number of undesired secondary effects arise, such as sunburn or premature skin ageing and the development of wrinkles. In the meantime, a number of performance UV filters have been developed which, applied to the skin in the form of creams, lotions or gels, can effectively delay the development of sunburn even when the incidence of solar rays is relatively high. The UV filter present in the pharmaceutical or cosmetic composition forms a film or a layer on the surface of the skin and does not penetrate into deeper skin layers with other care substances present in the composition. Known UV filters or sun protection agents thus act only by absorbing certain regions of sunlight, meaning that this radiation cannot penetrate into deeper layers of the skin. As is known, the most hazardous part of solar radiation is formed by the ultraviolet rays having a wavelength of less than 400 nm. The lower limit of the ultraviolet rays which reach the surface of the earth is limited by the absorption in the ozone layer to about 280 nm. The sun protection filters which are nowadays customary in cosmetics absorb in a wavelength range from 280 to 400 nm. This range includes UV-B rays having a wavelength between 280 and 320 nm, which play a decisive role in the formation of a solar erythema, and also UV-A rays, having a wavelength between 320 and 400 nm, which tan the skin but also age it, favour the triggering of an erythematous reaction or can exacerbate this reaction in certain people or even trigger phototoxic or photoallergic and irritative reactions.

The object of care cosmetics is wherever possible to obtain the impression of a youthful skin. In principle, there are various ways of achieving this object. For example, existing skin damage, such as irregular pigmentation or the development of wrinkles can be smoothed out by covering powders or creams. Another approach is to protect the skin against environmental influences which lead to permanent damage and thus ageing of the skin. The idea is therefore to intervene in a preventative manner and thus to delay the ageing process. One example of this is the UV filters already mentioned which, as a result of absorption of certain wavelength regions, prevent or at least reduce skin damage. Depending on the position of their absorption maxima, UV absorbers for cosmetic and dermatological compositions are divided into UV-A and UV-B absorbers. UV-A absorbers are usually also absorbing in the UV-B region and thus alternatively also being referred to as broad-band absorbers or broad-band filters.

It is known that inorganic UV filters such as Titanium dioxide do not penetrate the skin, while several sunscreen compositions comprising soluble organic UV filters are said to penetrate the skin. Furthermore it is desired to induce a protective UV absorbing layer on top of the skin's surface in order to prevent any possible interactions of the applied filters with the skin.

Therefore there was a need for formulations with high Sun Protection Factor which are less penetrating the skin.

A first embodiment of our invention therefore is a composition having UV protection properties, characterised in that the formulation comprises at least one encapsulated organic sunscreen and does not penetrate the skin essentially.

Preferably the at least one encapsulated organic sunscreen is encapsulated in capsules mainly consisting of organic polymeric materials and/or inorganic oxidic materials.

Suitable capsules can have walls made of inorganic or organic polymers. For example, U.S. Pat. No. 6,242,099 B1 describes the preparation of suitable capsules with balls made of chitin, chitin derivatives or polyhydroxylated polyamines. Capsules which are to be used particularly preferably according to the invention have walls which can be obtained by a sol-gel process, as is described in the applications WO 00/09652, WO 00/72806 and WO 00/71084. Preference is given here in turn to capsules whose walls are made of silica gel (silica; undefined silicon oxide hydroxide). The preparation of corresponding capsules is known to the person skilled in the art, for example, from the cited patent applications, the contents of which also expressly belonging to the subject-matter of the present application.

Here, the capsules are present in formulations according to the invention preferably in amounts which ensure that the encapsulated UV filters are present in the formulation in the typical amounts given below.

The minimal particle size of those capsules depends on necessary size to prevent penetration of the skin. On the other side, the maximum particle size is limited by the application needs. The capsules shouldn't be discernible with blank eyes. Preferred capsules have a average particle size in the range from about 10 nm up to about 10000 nm, preferably up to 5000 nm and most preferred up to 2000 nm.

The compositions according to our invention do not penetrate the skin essentially. This means the compositions do penetrate the skin in a lower amount than conventional compositions comprising soluble organic UV filters which are not encapsulated. The penetration can for example be measured according to COLIPA (The European Cosmetic Toiletry and Perfumery Association); 1997; Guidelines; "Cosmetic ingredients: Guidelines for percutanous absorption/penetration" with a Franz type Diffusion Cell or according to Weigmann et al. in Skin Pharmacol. Appl. Skin Physiol. 12 (1999) 34-45. Preferred compositions of our invention show a reduction of skin penetration measured with at least one of this methods of at least 10% preferably at least 20% and even more preferred at least 50% compared to compositions with the same but unencapsulated UV filters.

In principle, all known UV filters are suitable for compositions according to our invention. The filters can preferably be included either in solid, dispersed or in encapsulated form. All organic UV-filters mentioned in the list below are preferred as encapsulated filters. Especially preferred are 2-Ethylhexl-Methoxy Cinnamaic-Acid and/or 2-ethylhexyl-2-cyano-3,3-diphenylacrylate combined with Butylmethoxy Dibenzoylmethane and/or 2-ethylhexyl-2-cyano-3,3-diphenylacrylate, Homomethyl Salicylate or Octyl Salicylate alone or in combination with other filters.

In one preferred embodiment of our invention the composition comprises no organic sunscreen agents in soluble form. In another preferred embodiment the compositions contain an amount of water soluble organic UV filters, preferably selected from 2-phenylbenzimidazole-5-sulfonic acid, and its potassium, sodium and triethanolamine salts (e.g. Eusolex® 232) or Disodium Phenyl Dibenzimidazole Tetrasulfonate (e.g. Neoheliopan® AP).

In preferred compositions at least one organic sunscreen is immobilised by being coupled to a surface or a polymeric chain, preferably to the surface of inorganic sunscreen particles and/or a siloxane polymeric chain. The coupling of UV filters to surfaces is for example described in the pending German patent applications DE 10055588.8 and DE 10055469.5. According to these patent applications, that are explicitly included by reference in here, the UV filters are coupled via functional groups and preferably via spacer groups to an inorganic surface, preferably a silicon or titanium dioxide surface. Also preferred are compositions that comprise at least one polymeric UV filter. Polymeric UV filters are those polymers with UV filtering properties in the main chain. The chemical attaching of UV filters to polymeric chains, preferably siloxane chains is for example described in EP-A-0709080, EP-A-0982310 and EP-A-0933376. One especially preferred UV filter attached to a siloxan chain is Dimethico-diethyl-benzal-malonate.

In a further preferred embodiment the compositions comprise at least one micronized organic UV filter, preferably selected from triazin derivatives, benzotriazole derivatives, vinyl group-containing amide derivatives, cinnamic acid amide derivatives and/or sulfonated benzimidazole derivatives, most preferred from triazin derivatives. Those micronized organic UV filters are for example described in WO 99/66896 and WO 00/78277, included by reference herein. A preferred example for micronized UV filters is 2,2'-methylen-bis-[6-(2H-benztriazol-2-yl)-4-/1,1,3,3-tetramethylbutyl)-phenol (e.g. Tinsorb™ M).

In general all known organic UV filters may be encapulated or immobilzed according to our invention. Particular preference is given to those UV filters whose physiological safety has already been demonstrated. There are many tried and tested substances known from the specialist literature for both UVA and also UVB filters, e.g.

Benzylidenecamphor derivatives, such as
  3-(4'-methylbenzylidene)-dl-camphor (e.g. Eusolex® 6300),
  3-benzylidenecamphor (e.g. Mexoryl® SD),
  polymers of N-{(2 and 4)-[(2-oxoborn-3-ylidene)methyl]benzyl}acrylamide (e.g. Mexoryl® SW),
  N,N,N-trimethyl-4-(2-oxoborn-3-ylidenemethyl) anilinium methylsulfate (e.g. Mexoryl® SK) or
  α-(2-oxoborn-3-ylidene)toluene-4-sulfonic acid (e.g. Mexoryl® SL), benzoyl- or dibenzoylmethanes, such as
  1-(4-tert-butylphenyl)-3-(4-methoxyphenyl)propane-1,3-dione (e.g. Eusolex® 9020) or
  4-isopropyldibenzoylmethane (e.g. Eusolex® 8020), benzophenones, such as
  2-hydroxy-4-methoxybenzophenone (e.g. Eusolex® 4360) or
  2-hydroxy-4-methoxybenzophenone-5-sulfonic acid and its sodium salt (e.g. Uvinul® MS-40), 4,4,-diarylbutadienes as described in EP-A-0 916 335, methoxycinnamic esters, such as
  octyl methoxycinnamate (e.g. Eusolex® 2292),
  isopentyl 4-methoxycinnamate, e.g. as a mixture of the isomers (e.g. Neo Heliopan® 1000), salicylate derivatives, such as
  2-ethylhexyl salicylate (e.g. Eusolex® OS),
  4-isopropylbenzyl salicylate (e.g. Megasol®) or
  3,3,5-trimethylcyclohexyl salicylate (e.g. Eusolex® HMS), 4-aminobenzoic acid and derivatives, such as
  4-aminobenzoic acid,
  2-ethylhexyl 4-(dimethylamino)benzoate (e.g. Eusolex® 6007),
  ethoxylated ethyl 4-aminobenzoate (e.g. Uvinul® P25), diphenylacrylates, e.g. 2-ethylhexyl-2-cyano-3,3-diphenylacrylate (Eusolex® OCR)

and further substances, such as 2-phenylbenzimidazole-5-sulfonic acid, and its potassium, sodium and triethanolamine salts (e.g. Eusolex® 232), 3,3'-(1,4-phenylenedimethylene)-bis(7,7-dimethyl-2-oxobicyclo[2.2.1]hept-1-ylmethanesulfonic acid and its salts (e.g. Mexoryl® SX), 2,4,6-trianilino-(p-carbo-2'-ethylhexyl-1'-oxy)-1,3,5-triazine (e.g. Uvinul® T 150) and 2-(4-Diethylamino-2-hydroxy-benzoyl)-benzoic acid hexyl ester (e.g. Uvinul® A Plus, BASF).

The compounds given in the list are only to be regarded as examples. It is of course also possible to use other UV filters.

Further suitable organic UV filters are, for example, 2-(2H-benzotriazol-2-yl)-4-methyl-6-(2-methyl-3-(1,3,3,3-tetramethyl-1-(trimethylsilyloxy)disiloxanyl)propyl)phenol (e.g. Silatrizole®), bis(2-ethylhexyl) 4,4'-[(6-[4-((1,1-dimethylethyl)aminocarbonyl)-phenylamino]-1,3,5-triazine-2,4-diyl)diimino]bisbenzoate (e.g. Uvasorb® HEB), α-(trimethylsilyl)-ω-[trimethylsilyl)oxy]poly[oxy(dimethyl [and about 6% methyl[2-[p-[2,2-bis(ethoxycarbonyl)vinyl]phenoxy]-1-methylenethyl] and about 1.5% methyl[3-[p-[2,2-bis(ethoxycarbonyl)vinyl]phenoxy)propenyl) and 0.1 to 0.4% (methyl-hydrogen]silylene]] (n≈60) (CAS No. 207 574-74-1), 2,2'-methylenebis(6-(2H-benzotriazol-2-yl)-4-(1,1,3,3-tetramethylbutyl)phenol) (CAS No. 103 597-45-1), 2,2'-(1,4-phenylene)bis(1H-benzimidazol-4,6-disulfonic acid, monosodium salt) (CAS No. 180 898-37-7) and 2,4-bis{[4-(2-ethylhexyloxy)-2-hydroxyl]phenyl}-6-(4-methoxy-phenyl)-1,3,5-triazine (CAS No.103 597-45-, 187 393-00-6).

These UV filters are usually incorporated into cosmetic formulations in an amount of from 0.5 to 20% by weight, preferably 1-15%.

Conceivable as inorganic UV filters are those from the group of titanium dioxides, such as, for example, coated titanium dioxide (e.g. Eusolex® T-2000, Eusolex® T-AQUA), zinc oxides (e.g. Sachtotec®), iron oxides and also cerium oxides. These inorganic UV filters are generally incorporated into cosmetic formulations in an amount of from 0.5 to 20% by weight, preferably 2-10%.

Preferred compounds with UV-filtering properties are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid, its potassium, sodium and triethanolamine salts and coated titanium dioxide.

By combining two or more compounds listed above it is possible to optimize the protective action against harmful effects of UV radiation. The combination of the above-mentioned UV filters in a formulation gives a composition which combines light protection with particular mildness to the skin. All of the UV filters specified can be used in encapsulated or in immobilized form as described above.

It is also preferred, if the composition comprises at least one inorganic sunscreen agent, preferably at least one microparticulate inorganic sunscreen, most preferably selected from zink or titanium dioxide.

It is therefore preferred according to the invention if one or more of the above-mentioned UV filters are present in encapsulated form. In this connection, it is advantageous if the capsules are so small that they can not be observed with the naked eye. To achieve the above-mentioned effects, it is also necessary for the capsules to be sufficiently stable and not to release the encapsulated active ingredient (UV filter) into the surroundings, or to release it only to a slight extent.

Advantages of the compositions according to our invention are:

High Sun protection factor (SPF).
Good photostability of the composition.
No or low penetration of the skin Another embodiment of our invention therefore is the use of sunscreen capsules to prevent sunscreens form penetration of the skin.

The performance of a cosmetic formulation according to the SPF is influenced by the distribution of the UV filters on the surface of the skin or within the upper corneocyte layers. Therefore the rheology of the formulation is a key issue to increase the SPF (boost effect). According to the theory, applied cosmetic vehicles fill up the furrows easily while the ridges are not covered efficiently by the formulations in many cases. A further advantage of the formulations comprising Sunscreen capsules is that they cover both the furrows as well as the ridges of the skin which is due to their rheological influence on cosmetic formulations. This enables the formulation to build up a more uniform layer on top of the skin's surface. Due to this SPF boost effect of sunscreen capsules formulations comprising the sunscreen capsules are supposed to show a higher SPF value compared to formulations without such capsules but the same amount of UV filters. Therefore another embodiment of our invention is the use of capsules to increase the SPF value of a given sunscreen formulation.

The protecting action against oxidative stress or against the effect of free radicals can be further improved if the formulation comprises one or more antioxidants.

There are many tried and tested substances known from the specialist literature which can be used, e.g. amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glycerylesters thereof, and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine-sulfoximine, homocysteine-sulfoximine, buthionine-sulfone, penta-, hexa- and heptathionine-sulfoximine) in very low tolerated doses (e.g. pmol to µmol/kg), and also (metal) chelating agents, (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate), and coniferyl benzoate of benzoin resin, rutin and salts of the sulfuric ester of rutin and derivatives thereof, α-glycosyl rutin, ferulic acid, furfurylidineglucitol, carosine, butylhydroxytoluene, butylhydroxyanisol, nordihydroguaretic acid, trihydroxybutyrophenone, quercetin, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide).

Mixtures of antioxidants are likewise suitable for use in the cosmetic formulations according to the invention. Known and commercial mixtures are, for example, mixtures comprising, as active ingredients, lecithin, L-(+)-ascorbyl palmitate and citric acid (e.g. Oxynex® AP), natural tocopherols, L-(+)-ascorbyl palmitate, L-(+)ascorbic acid and citric acid (e.g. Oxynex® K LIQUID), tocopherol extracts from natural sources, L-(+)-ascorbyl palmitate, L-(+)-ascorbic acid and citric acid (e.g. Oxynex® L LIQUID), DL-α-tocopherol, L-(+)-ascorbyl palmitate, citric acid and lecithin (e.g. Oxynex® LM) or butylhydroxytoluene (BHT), L-(+)-ascorbyl palmitate and citric acid (e.g. Oxynex® 2004).

The formulations according to the invention can comprise vitamins as further ingredients. Preferably, vitamins and vitamin derivatives chosen from vitamin A, vitamin A propionate, vitamin A palmitate, vitamin A acetate, retinol, vitamin B, thiamine chloride hydrochloride (vitamin $B_1$), riboflavin (vitamin $B_2$) nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$) nicotinic acid (niacin), pyridoxine, pyridoxal, pyridoaxmine, (vitamin $B_6$), panthothenic acid, biotin, folic acid and cobalamine (vitamin $B_{12}$) are present in the cosmetic formulations according to the invention, particularly preferably vitamin A palmitate, vitamin C, DL-α-tocopherol, tocopherol E acetate, nicotinic acid, panthothenic acid and biotin.

The composition of our invention can be a cosmetic formulation or a pharmaceutical formulation.

Examples of application forms of the cosmetic or pharmaceutical formulations according to the invention which may be mentioned are: solutions, suspensions, emulsions, PIT emulsions, pastes, ointments, gels, creams, lotions, powders, soaps, foams, surfactant-containing cleansing preparations, oils, aerosols and sprays. Examples of other application forms are sticks, shampoos and shower preparations. Any customary carriers, auxiliaries and optionally further active ingredients may be added to the formulation.

Preferred auxiliaries originate from the group of preservatives, antioxidants, stabilizers, solubility promoters, vitamins, colorants, odour improvers.

Ointments, pastes, creams and gels may comprise the customary carriers, e.g. animal and vegetable fats, waxes, paraffins, starch, tragacanth, cellulose derivatives, polyethylene glycols, silicones, bentonites, silica, talc and zinc oxide or mixtures of these substances.

Powders and sprays may comprise the customary carriers, e.g. lactose, talc, silica, aluminium hydroxide, calcium silicate and polyamide powder or mixtures of these substances. Sprays can additionally comprise customary propellants, e.g. chlorofluorocarbons, propane/butane or dimethyl ether.

Solutions and emulsions can comprise the customary carriers, such as solvents, solubility promoters and emulsifiers, e.g. water, ethanol, isopropanol, ethyl carbonate, ethyl acetate, benzyl alcohol, benzyl benzoate, propylene glycol, 1,3-butylglycol, oils, in particular cotton seed oil, peanut oil, wheatgerm oil, olive oil, castor oil and sesame oil, glycerol fatty acid ester, polyethylene glycols and fatty acid esters of sorbitan or mixtures of these substances.

Suspensions can comprise the customary carriers such as liquid diluents, e.g. water, ethanol or propylene glycol, suspending agents, e.g. ethoxylated isostearyl alcohols, polyoxyethylene sorbitol esters and polyoxyethylene sorbitan esters, microcrystalline cellulose, aluminium metahydroxide, bentonite, agar agar and tragacanth or mixtures of these substances.

Soaps can comprise the customary carriers, such as alkali metal salts of fatty acids, salts of fatty acid mono esters, fatty acid protein hydrolysates, isethionates, lanolin, fatty alcohol, vegetable oils, plant extracts, glycerol, sugars or mixtures of these substances.

Surfactant-containing cleansing products can comprise the customary carrier substances, such as salts of fatty alcohol sulfates, fatty alcohol ether sulfates, sulfosuccinic monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters or mixtures of these substances.

Face and body oils can comprise the customary carrier substances such as synthetic oils, such as fatty acid esters, fatty alcohols, silicone oils, natural oils, such as vegetable oils and oily plant extracts, paraffin oils, lanolin oils or mixtures of these substances.

Further typically cosmetic application forms are also lipsticks, lipcare sticks, mascara, eyeliner, eyeshadow, blusher, powder make-up, emulsion make-up and wax make-up, and sunscreen, presun and aftersun preparations.

All compounds or components which can be used in the cosmetic formulations are either known and available commercially or can be synthesized by known processes.

As dispersant or solubilizer it is possible to use an oil, wax or other fatty substance, a lower monoalcohol or a lower polyol or mixtures thereof. Preferred monoalcohols or polyols include ethanol, isopropanol, propylene glycol, glycerol and sorbitol.

A preferred embodiment of the invention is an emulsion in the form of a protective cream or milk and which comprise, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The cosmetic preparation according to the invention can also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

Preferred compositions of our invention are hydrogels. The hydrophilicity of the capsule wall can be set independently of the solubility of the UV filter. For example, it is possible to incorporate even hydrophobic UV filters into purely aqueous formulations. Due to this possibility to include high amounts of hydrophobic UV filters in encapsulated or immobilized form, as described above, those hydrogels of our inventions can posses high SPF values, in a range normally only acheived with oily formulations.

The solid sticks consist of natural or synthetic waxes and oils, fatty alcohols, fatty acids, fatty acid esters, lanolin and other fatty substances.

All compounds or components which can be used in the cosmetic or pharmaceutical formulations are either known and available commercially or can be synthesized by known processes.

The composition according to the invention is particularly suitable for protecting human skin against the harmful influences of the UV constituents in sunlight, in addition they also offer protection against ageing processes of the skin and against oxidative stress, i.e. against damage caused by free radicals, as are produced, for example, by solar irradiation, heat or other influences.

Therefore the use of a composition according to our invention for the manufacture of a medicament suitable for the prophylaxis of damages of the skin caused by sunray, especially for the prophylaxis of sunburn and sun-caused erythrema is another embodiment of our invention. A further embodiment is the cosmetic prophylaxis of damages of the skin caused by sunray, especially for the prophylaxis of sunburn and sun-caused erythrema.

The formulation may comprise adjuvants which are customarily used in this type of composition, such as, for example, thickeners, softeners, moisturizers, surface-active agents, emulsifiers, preservatives, perfumes, waxes, lanolin, propellants, dyes and/or pigments which colour the composition itself or the skin, and other ingredients customarily used in cosmetics.

The composition may be a foamable composition able to be foamed up with or without an propellant. According to our invention it is especially preferred if the foam is produced without the use of a organic propellant. Sprays using organic propellents may not be stored in direct sun or at higher temperatures; conditions that for example can often be found on the beach during summer. An advantage of preferred compositions according to our invention is that the may be stored and used even under these conditions.

Preferred compositions are included in a foam dispenser, preferably in a foam dispenser that requires no organic propellant as described above.

As foam builders/stabilisers in general all substances able to build or stabilise a foam may be used. Those substances in general are known to those skilled in the art. Preferred foam builders/stabilisers are those which are skin tolerant or even more preferably give a benefit to the skin.

The foam builders/stabilisers are usually present in an amount of about 0.01 to 20% by weight, preferably in an amount of 0.1 to 5% by weight and even more preferred in an amount of 0.1 to 3% by weight.

Preferred foam builders/stabilisers are cetyl phosphate, DEA cetyl phosphate, TEA myristate, TEA stearate, magnesium stearate, sodium stearate, potassium laurate, potassium ricinoleate, sodium cocoate, sodium tallowate, potassium castorate, sodium oleate and mixtures thereof.

Other preferred foam stabilisers are so called foam boosters. Foam boosters are substances which increase the surface viscosity of the liquid which surrounds the individual bubbles in a foam. These agents are commonly used in shaving soaps, shampoos, bubble baths, liquid soaps, mousses, or aerosol-dispensed foams. Also Film Formers or Viscosity-Increasing Agents maybe used as foam boosters. The listing below gives examples for foam boosters which can also be classified as surfactants (INCI names):

Acetamide MEA, Almondamide DEA, Almondamidopropylamine Oxide, Almondamidopropyl Betaine, Apricotamide DEA, Apricotamidopropyl Betaine, Avocadamide DEA, Avocadamidopropyl Betaine, Babassuamide DEA, Babassuamidopropylamine Oxide, Babassuamidopropyl Betaine, Behenamide DEA, Behenamide MEA, Behenamidopropyl Betaine, Behenamine Oxide, Behenyl Betaine, Canolamidopropyl Betaine, Capramide DEA, Carnitine, Cetearyl Alcohol, Cetyl Alcohol, Cetyl Betaine, Cocamide DEA, Cocamide MEA, Cocamide MIPA, Cocamidoethyl Betaine, Cocamidopropylamine Oxide, Cocamidopropyl Betaine, Cocamidopropyl Hydroxysultaine, Cocamine Oxide, Cocoamphodipropionic Acid, Cocobetainamido Amphopropionate, Coco-Betaine, Coco-Hydroxysultaine, Coco-Morpholine Oxide, Coconut Alcohol, Coco/Oleamidopropyl Betaine, Coco-Sultaine, Cocoyl Sarcosinamide DEA, DEA-Cocoamphodipropionate, DEA-Lauraminopropionate, Decyl Alcohol, Decylamine Oxide, Decyl Betaine, Diethanolaminooleamide DEA, Dihydroxyethyl C8-10 Alkoxypropylamine Oxide, Dihydroxyethyl C9-11 Alkoxypropylamine Oxide, Dihydroxyethyl C12-15 Alkoxypropylaminde Oxide, Dihydroxyethyl Cocamine Oxide, Dihydroxyethyl Lauramine Oxide, Dihydroxyethyl Stearamine Oxide, Dihydroxyethyl Tallowamine Oxide, Dimethicone Propyl PG-Betaine, Disodium Caproamphodiacetate, Disodium Caproamphodipropiante, Disodium Capryloamphodiacetate, Disodium Capryloamphodipropionate, Disodium Cetearyl SulfosuccinateDisodium Cocamido MIPA-Sulfosuccinate, Disodium Cocamido PEG-3 Sulfosuccinate, Disodium Cocaminopropyl Iminodiacetate, DisodiumCocoamphocarboxyethylhydroxypropylsulfonate, Disodium Cocoamphodiacetate, Disodium Cocoamphodipropionate, Disodium C12-15 Pareth Sulfosuccinate, Disodium Deceth-5 Sulfosuccinate, Disodium Deceth-6 Sulfosuccinate, Disodium Hydrogenated Cottonseed Glyceride Sulfosuccinate, Disodium Isodecyl Sulfosuccinate, Disodium Isostearamido MEA-Sulfosuccinate, Disodium Isostearamido MlPA-Sulfosuccinate, Disodium Isostearoamphodiacetate, Disodium Isostearoamphodipropionate, Disodium Isostearyl Sulfosuccinate, Disodium Laneth-5 Sulfosuccinate, Disodium Lauramido MEA-Sulfosuccinate, Disodium Lauramido PEG-2 Sulfosuccinate, Disodium Laureth-5 Carboxyamphodiacetate, Disodium Laureth Sulfosuccinate, Disodium Laureth-6 Sulfosuccinate, Disodium Laureth-9 Sulfosuccinate, Disodium Laureth-12 Sulfosuccinate, Disodium Lauroamphodiacetate, Disodium Lauroamphodipropiante, Disodium Lauryl Sulfosuccinate, Disodium Myristamido MEA-Sulfosuccinate, Disodium Nonoxynol-10 Sulfosuccinate, Disodium Oleamido MEA-Sulfosuccinate, Disodium Oleamido MIPA-Sulfosuccinate, Disodium Oleamido PEG-2 Sulfosuccinate, Disodium Oleoamphodipropionate, Disodium Oleth-3 Sulfosuccinate, Disodium Oleyl Sulfosuccinate, Disodium Palmitamido PEG-2 Sulfosuccinate, Disodium Palmitoleamido PEG-2 Sulfosuccinate, Disodium PEG4 Cocamido MIPA-Sulfosuccinate, Disodium PPG-2-Isodeceth-7 Carboxyamphodiacetate, Disodium Ricinoleamido MEA-Sulfosuccinate, Disodium Stearamido MEA-Sulfosuccinate, Disodium Stearamphodiacetate, Disodium Stearyl Sulfosuccinamate, Disodium Stearyl Sulfosuccinate, Disodium Tallamido MEA-Sulfosuccinate, Disodium Tallowamido MEA-Sulfosuccinate, Disodium Tallowamphodiacetate, Disodium Tallow Sulfosuccinamate, Disodium Tridecylsulfosuccinate, Disodium Undecylenamido MEA-Sulfosuccinate, Disodium Undecylenamido PEG-2 Sulfosuccinate, Disodium Wheat Germamido MEA-Sulfosuccinate, Disodium Wheat Germamido PEG-2 Sulfosuccinate, Disodium Wheatgermamphodiacetate, Di-TEA-Oleamido PEG-2 Sulfosuccinate, Ditridecyl Sodium Sulfosuccinate, Erucamidopropyl Hydroxysultaine, Hydrogenated Tallow Alcohol, Hydrogenated Tallowamide DEA, Hydrogenated Tallowamine Oxide, Hydrogenated Tallow Betaine, Hydroxyethyl Carboxymethyl Cocamidopropylamine, Hydroxethly Hydroxypropyl C12-15 Alkoxypropylamine Oxide, Hydroxystearamide MEA, Isostearamide DEA, Isostearamide MEA, Isostearamide MIPA, Isostearamidopropylamine Oxide, Isostearamidopropyl Betaine, Isostearamidopropyl Morpholine Oxide, Lactamide MEA, Lanolinamide DEA, Lauramide DEA, Lauramide MEA, Lauramide MIPA, Lauramide/Myristamide DEA, Lauramidopropylamine Oxide, Lauramidopropyl Betaine, Lauramine Oxide, Lauroamphodipropionic Acid, Lauryl Alcohol, Lauryl Betaine, Lauryl Hydroxysultaine, Lauryl Sultaine, Lecithinamide DEA, Linoleamide DEA, Linoleamide MEA, Linoleamide MIPA, Methyl Morpholine Oxide, Minkamide DEA, Minkamidopropylamine Oxide, Minkamidopropyl Betaine, Myristamide DEA, Myristamide MEA, Myristamide MIPA, Myristamidopropylamine Oxide, Myristamidopropyl Betaine, Myristamine Oxide, Myristaminopropionic Acid, Myristyl Alcohol, Myristyl Betaine, Myristyl/Cetyl Amine Oxide, Oleamide DEA, Oleamide MEA, Oleamide MIPA, Oleamidopropylamine Oxide, Oleamidopropyl Betaine, Oleamidopropyl Hydroxysultaine, Oleamine Oxide, Oleyl Betaine, Olivamide DEA, Olivamidopropylamine Oxide, Olivamidopropyl Betaine, Palmamide DEA, Palmamide MEA, Palmamide MIPA, Palmamidopropyl Betaine, Palmitamide DEA, Palmitamide MEA, Palmitamidopropylamine Oxide, Palmitamidopropyl Betaine, Palmitamine Oxide, Palm Kernel Alcohol, Palm Kernelamide DEA, Palm Kernelamide MEA, Palm Kernelamide MIPA, Palm Kernelamidopropyl Betaine, Peanutamide MEA, Peanutamide MIPA, PEG-3 Cocamide, PEG-2 Hydrogenated Tallow Amine, PEG-3 Lauramide, PEG-3 Lauramide Oxide, PEG-2 Oleamide, PEG-3 Oleamide, PEG-2 Oleamine, PEG-2 Soyamine, PEG-2 Stearamine, Potassium Dihydroxyethyl Cocamine Oxide Phosphate, Ricinoleamide DEA, Ricinoleamide MEA, Ricinoleamide MIPA, Ricinoleamidopropyl Betaine, Sesamide DEA, Sesamidopropylamine Oxide, Sesamidopropyl Betaine, Sodium Caproamphoacetate, Sodium Caproamphohydroxy-propylsulfonate, Sodium Caproamphopropionate, Sodium Capryloamphoacetate, Sodium Capryloamphohydroxypropylsulfonate, Sodium Capryloamphoproprionate, Sodium Cocoamphoacetate, Sodium Cocoamphohydroxypropylsulfonate, Sodium Cocoamphopropionate, Sodium Cornamphopropionate, Sodium Isostearoampho-acetate, Sodium Isostearoamphopropionate, Sodium Lauramidopropyl Hydroxyphostaine, Sodium Lauraminopropionate, Sodium Lauriminodipropionate, Sodium Lauroamphoacetate, Sodium/MEA Laureth-2 Sulfosuccinate, Sodium Myristoamphoacetate, Sodium Oleoamphoacetate, Sodium Oleoamphohydroxy-propylsulfonate, Sodium Oleoamphopropionate, Sodium Ricinoleoamphoacetate, Sodium Stearoamphoacetate, Sodium Stearoamphohydroxypropylsulfonate, Sodium Stearoamphopropionate, Sodium Tallamphopropionate, Sodium Tallowamphoacetate, Sodium Tallowate, Sodium Undecylenoamphoacetate, Sodium Undecylenoamphopropionate, Sodium Wheat Germamphoacetate, Soyamide DEA, Soyamidopropyl Betaine, Stearamide AMP, Stearamide DEA, Stearamide DEA-Distearate, Stearamide MEA, Stearamide MEA-Stearate, Stearamide MIPA, Stearamidopropylamine Oxide, Stearamidopropyl Betaine, Stearamine Oxide, Stearyl Alcohol, Stearyl Betaine, Tallamide DEA, Tallowamide DEA, Tallowamide MEA, Tallowamidopropylamine Oxide, Tallowamidopropyl Betaine, Tallowamidopropyl Hydroxysultaine, Tallowamine Oxide, Tallow Betaine, TEA-Lauraminopropionate, TEA-Myristaminopropionate, Trideceth-2 Carboxamide MEA, Trisodium Lauroampho PG-Acetate Phosphate Chloride, Undecylenamide DEA, Undecylenamide MEA, Undecylenamidopropylamine Oxide, Undecylenamidopropyl Betaine, Wheat Germamide DEA, Wheat Germamidopropylamine Oxide, Wheat Germamidopropyl Betaine.

In another embodiment at least one foam builder/stabiliser is selected from foaming surfactants, preferably from alkylglyosides, anionic protein derivatives or fatty acid sulfonates.

An especially preferred foam builder/stabilisers are anionic protein derivatives, such as lipoaminoacids described in WO 98/09611, WO 99/27902 and WO 99/45899. Most preferred under these anionic protein derivatives are sodium lauroyl oat amino acids, for example known as Proteol™ Oat (Tradename of Seppic).

The cosmetic formulation can also be used to protect the hair against photochemical damage in order to prevent changes of colour shades, decoloration or damage of a mechanical nature. In this case, a suitable formulation is in the form of a shampoo or lotion for rinsing out, the formulation in question being applied before or after shampooing, before or after colouring or bleaching or before or after permanent waving. It is also possible to choose a formulation in the form of a lotion or gel for styling or treating the hair, in the form of a lotion or gel for brushing or blow-waving, in the form of a hair lacquer, permanent waving composition, colorant or bleach for the hair. The cosmetic formulation may comprise various adjuvants used in this type of composition, such as surface-active agents, thickeners, polymers, softeners, preservatives, foam stabilizers, electrolytes, organic solvents, silicone derivatives, anti-grease agents, dyes and/or pigments which colour the composition itself or the hair, or other ingredients customarily used for hair care.

To protect the skin and/or natural or sensitized hair against solar rays, the cosmetic composition is applied to the skin or the hair. Sensitized hair is understood here as meaning hair which has been subjected to a chemical treatment, such as a permanent waving treatment, a colouring process or bleaching process.

The compositions of our invention can be produced by by mixing dispersions of insuloble and/or encapsulated sunscreens and/or dispersions of inorganic sunscreen particles with other ingredients of the composition.

The examples below illustrate the present invention in more detail without limiting the scope of the invention. The following trade names are used in the example formulations:

EXAMPLES

The silica capsules used in the examples (Eusolexo® UV-Pearls™) are obtained by a sol-gel process, as is described in the applications WO 00/09652, WO 00/72806 and WO 00/71084. The preparation of corresponding capsules is known to the person skilled in the art, for example, from the cited patent applications, the contents of which also expressly belonging to the subject-matter of the present application.

UV Pearls™ in the examples means an aqueous dispersion of silica capsules comprising about 33% by weight of UV filters.

Abbreviations:
BMDBM butyl methoxydibenzoylmethane
BP-3 benzophenone-3
OCR 2-ethylhexyl-2-cyano-3,3-diphenylacrylate
OMC octyl methoxycinnamate Example 1

Photo-acoustic in vivo Investigation of the Stratum Corneum

Method

The photo-acoustic method (Puccetti G, Leblanc R M: Photoacoustic spectroscopy of sunscreens applied to human skin: Towards the in situ monitoring of filter penetration and interaction in the different layers of the skin. *Recent Res. Devel. Photochem. & Photobiol*, 5: 79-93 (2001); Imhof R E, Whitters C J, Birch D J S: Opto-thermal in vivo monitoring of sunscreens on skin. *Phys. Med. Biol.*, 35: 95-102 (1990); Giese K, Nicolaus A, Sennhenn B, Külmel K: Photoacoustic in vivo study of the penetration of sunscreens into human skin. *Can. J. Phys.*, 64: 1139-1141 (1986)) is based on a widespread phenomenon: light absorbed by a material is partly re-emitted as heat. Energy from a light source is transferred to a sample via light absorption and partially re-emitted as heat, which is then detected by a sensor. Under pulsed light conditions (e.g. laser), a sample will generate a pulse of heat release.

Human skin absorbs light in the UV range, which is therefore used as source of light. Typical photo-acoustic studies involve near surface detection, i.e. typically 40-60 μm, within the limits of the maximal heat diffusion depth in skin.

The dermal uptake of a product applied to skin is assessed using photo-acoustics by monitoring the amplitude of the heat response. In the case of product applications to skin, molecules entering the skin are indicated by a decrease in the photo-acoustic heat response. This is due to the diffusion of molecules through the stratum corneum barrier layer and towards skin layers beyond 40-60 μm.

The dermal uptake of two formulations containing OMC (see Table 1) is measured after application to the forearm of a volunteer. The study is performed at two wavelengths of light: 266 nm to monitor the OMC (light is absorbed by OMC mostly) and 355 nm to observe formulation effects (light is mostly absorbed by the skin background). Energies of light irradiation are kept below erythema levels, at 0.8 mJ/cm$^2$ for 355 nm and 0.4 mJ/cm$^2$ for 266 nm.

Table 1: O/W lotion applied in vivo to human skin volunteers for photo-acoustic measurement of the skin. Both formulations contain 7% of OMC but one with free OMC, and the other as Eusolex® UV-Pearls™ OMC.

| CTFA/INCI | Free OMC % (w/w) | Eusolex ® UV-Pearls ™ % (w/w) |
|---|---|---|
| Ethylhexyl methoxycinnamate, BHT | 7.00 | — |
| Isopropyl myristate | 4.00 | 4.00 |
| C12-15 Alkyl benzoate | 4.00 | 4.00 |
| Cetyl alcohol | 1.50 | 1.50 |
| Steareth-2 | 2.00 | 2.00 |
| Steareth-21 | 2.50 | 2.50 |
| Dimethicone | 0.50 | 0.50 |
| Aqua (water) | 77.07 | 63.77 |
| Carbomer | 0.20 | 0.20 |
| Eusolex ® UV-Pearls ™ OMC | — | 20.03 |
| Triethanolamine | 0.23 | 0.23 |
| Phenoxyethanol, isopropylparaben, isobutylparaben, butylparaben | 1.00 | 1.00 |

The irradiation surface is 3×3 mm. Products are applied under identical conditions: 20 mg are spread over a circular area of 5 cm in diameter (~1 mg/cm$^2$). Data are the result of 3 experiments carried out under identical conditions, at 24 h intervals, on the forearm of a volunteer.

Results

The results show classical penetration dynamics for non-encapsulated OMC (FIG. 1). A regular signal decrease is observed at 266 nm over 2 hours, which reaches the signal value of skin without OMC. On the contrary, encapsulated OMC shows a short-term decrease (over 30 min), followed by an increase and subsequent stabilization at 90 min. This increase is contrary to penetration dynamics and indicates stable light absorption. Results at 355 nm confirm the surface presence of encapsulated OMC by reaching a long-term signal clearly higher than skin and characteristic of a permanent residue. Finally, the high photo-acoustic response of encapsulated OMC around 90-120 min confirms efficient UV absorption of the Eusolex® UV-Pearls™ and their excellent stability.

A comparison of OMC with Eusolex® UV-Pearls™ OMC shows a clearly different behavior on skin for the latter, opposite to classical penetration kinetics. While short-term formulation effects are observed for both products, the UV pearls show a signal increase for longer periods, which is typical of surface deposits.

Conclusion

In comparison to free UV filters, Eusolex® UV-Pearls™ have:
  A high and stable long-term photo-acoustic response leading to high UV absorption
  A long-term photo-acoustic response clearly higher than the skin (and formulation) representing surface presence of the Eusolex® UV-Pearls™ while non-encapsulated OMC has a significantly higher potential to enter the skin.

Example 2

Differential Stripping of the Stratum Corneum

The goal of this study was to determine and compare the distribution of OMC in the stratum corneum of two different formulations as applied to porcine skin, which serves as a model for in vivo human skin applications. The method used has been established (Weigmann H-J, Lademann J, Meffert H, Schaefer H, Sterry W: Determination of the horny layer profile by tape stripping in combination with optical spectroscopy in the visible range as a prerequisite to quantify percutaneous absorption. *Skin Pharmacol Appl Skin Physiol*, 12:34-45 (1999)) and is described below. This method is based on conventional stripping procedures combined with UV/VIS spectroscopy to determine both the substance, to be analyzed, and, in parallel, the weight of the comeocytes. This since it is possible to obtain the complete stratum corneum with this stripping procedure, the strips thus can be shown as a horny layer profile.

Method

Porcine ear skin is used due to its availability and well-known similarity to human skin. The horny layer had a thickness of about 20 μm. Two formulations are applied to an area of 20 cm$^2$ with a concentration of 2 mg/cm$^2$ (200 μg OMC/cm$^2$) and exposed for one hour. Both formulations contain 10% OMC but one with free OMC, and the other as Eusolex® UV-Pearls™ OMC (see Table 2). Afterwards, topical application and stripping was carried out using a standard procedure (The emulsion is applied with a syringe and evenly distributed with a gloved finger. After pressure application, all strips were removed from the marked area). The stripping is repeated as long as the spectral photometer has a transmission of 99.8% compared to the original tape strip as reference.

TABLE 2

Formulations applied to porcine skin for a comparative differential stripping experiment. Both formulations contain 10% OMC but one with free OMC, and the other as Eusolex ® UV-Pearls ™ OMC.

| CTFA/INCI | Free OMC % (w/w) | Eusolex ® UV-Pearls ™ % (w/w) |
|---|---|---|
| Phase A | | |
| Ethylhexyl methoxycinnamate, BHT | 10.00 | — |
| Steareth-10, Steareth-7, stearyl alcohol | 3.50 | 3.50 |
| Glyceryl stearate, Ceteth-20 | 3.00 | 3.00 |
| Glyceryl stearate | 3.00 | 3.00 |
| Microwax | 1.50 | 1.50 |
| Oleoyl oleate | 3.50 | 5.00 |
| Cetearyl octanoate | 8.00 | 16.00 |
| Caprylic/Capric triglyceride | 4.00 | 4.50 |
| Propylparaben | 0.05 | 0.05 |
| Phase B | | |
| Propylene glycol | 4.00 | 4.00 |
| Allantoin | 0.20 | 0.20 |
| Aqua (water) | 59.10 | 29.42 |
| Methylparaben | 0.15 | 0.15 |
| Phase C | | |
| Eusolex ® UV-Pearls ™ OMC | — | 29.68 |

After evaluation of the amount of stratum corneum photometrically at 900 nm, the strips are extracted with methanol, centrifuged and decanted. Amounts of OMC concentrations are calculated from the ratio peak area of the OMC to an internal OMC calibration curve. The detection limit for OMC is found to be 1 μg/ml±5%. The experiments are carried out in duplicate.

Results

Non-particulate substances lying in the furrows are distributed evenly due to the applied pressure—this releases the substances from the furrows, while particulate substances often remain. The differential stripping method with particles result more in a distribution profile on the skin than a profile in the stratum corneum (Amadine Amenc: Comparison of the penetraion of organic and inorganic UV filters used in sunscreens into the stratum corneum by applying the tape stripping method. Diploma-thesis, Ecole Nationale Supérieure de Chimie de Paris, and University Hospital Charité, Department of Dermatology and Allergy, Berlin, Germany (2001)); this has to be taken into account.

Both applied emulsions contain the same amount of UV filter, which has been confirmed by a very good total recovery of the applied 200 μg/cm$^2$. FIG. 2 shows the distribution profile in the outermost surface layers of the epidermal stratum corneum (SC). In the first strip, nearly 50% of the applied OMC is stripped off. After 10 strips, no further Eusolex® UV-Pearls™ OMC can be determined. At this stage, 25% of the SC are stripped off. This corresponds to a maximum depth of 5 μm where the OMC can be detected. We assume that the data given here for the Eusolex® UV-Pearls™ OMC are higher than reality due to the furrows of the skin.

However, on comparing these data with the free OMC (FIG. 3), we are able to determine significant differences within the first strips. Free OMC is distributed in the SC up to a depth of 15 μm (which corresponds to 75% of the SC and 1 μg/cm² in this strip).

Conclusion

Compared to free filters, Eusolex® UV-Pearls™ significantly reduce the uptake of UV filters by the skin. The encapsulated UV filters predominantly remain on the surface of the skin.

Example 3

Comparative Release Through an Inert Lipophilic Membrane

The goal of this study is to determine and compare the release of OMC from two different formulations through an inert lipophilic membrane which serves as a model (Jiang R, Benson H A E, Cross S E, Roberts M S. In vitro human epidermal and polyethylene membrane penetration and retention of sunscreen benzophenone-3 from a range of solvents. *Pharm. Res.*, 15: 1863-1886 (1998)) for in vitro human skin applications. (Jiang R, Robert M S, Prankerd R J, Benson H A E. Percutaneous absorption of sunscreen agents from liquid paraffin: self-association of octyl salicylate and effects on skin flux. *J. Pharm. Sci.*, 86: 791-796 (1997); Shah et al: In vitro release from corticosteorid ointments. *J. Pham. Sci.*, 84(9): 1139-1140 (1995); Jiang R, Robert M S, Prankerd R J, Benson H A E. Percutaneous absorption of sunscreen agents from liquid paraffin: self-association of octyl salicylate and effects on skin flux. *J. Pharm. Sci.*, 86: 791-796 (1997)).

Method

Two formulations are prepared, one with free, the other with encapsulated OMC. Both contained the same amount of OMC (see Table 3).

TABLE 3

Emulsion used for the comparative release experiment through an inert lipophilic membrane.

| CTFA/INCI | Free OMC % (w/w) | Eusolex ® UV-Pearls ™ % (w/w) |
|---|---|---|
| Phase A | | |
| Cetyl dimethicone copolyol | 2.2 | 3.0 |
| Isohexadecane | 6.8 | 9.5 |
| Cetearyl isononate | 5.6 | 7.75 |
| Octyl stearate | 5.6 | 7.75 |
| Ethylhexyl methoxycinnamate | 8.8 | — |
| Phase B | | |
| Sodium chloride | 1.0 | 1.0 |
| Glycerol | 4.0 | 4.0 |
| Eusolex ® UV-Pearls ™ OMC | — | 25.0 |
| Aqua (water) | 66.0 | 42.0 |

Tuffryn® membranes (200 nm in pore size) are soaked for 30 minutes in isopropyl myristate and blotted dry with tissue paper prior to use. The pre-treated membranes are mounted on a horizontal Franz diffusion cell with an application area of 1.3 cm². The receptor cell contains ca. 3.5 ml of phosphate-buffered saline (PBS), pH 7.4, 35° C., and 4% (w/v) bovine serum albumin. The receptor phase is continuously stirred with Teflon-coated magnets.

Each of the two formulations is applied to 3 separate cells, non-occluded, with a finite dose concentration of 5 mg/cm² (572 μg OMC/cell). The emulsions are gently spread over the entire surface of the membrane. The duration of the examination is 6 hours, 200 μl of the receptor phase is removed at specific points of time and replaced with an equal volume of fresh solution at each sampling.

Analysis is by HPLC, OMC concentrations are calculated from the ratio peak area of the OMC to an internal standard and calibration curve.

Results

Figure 4:
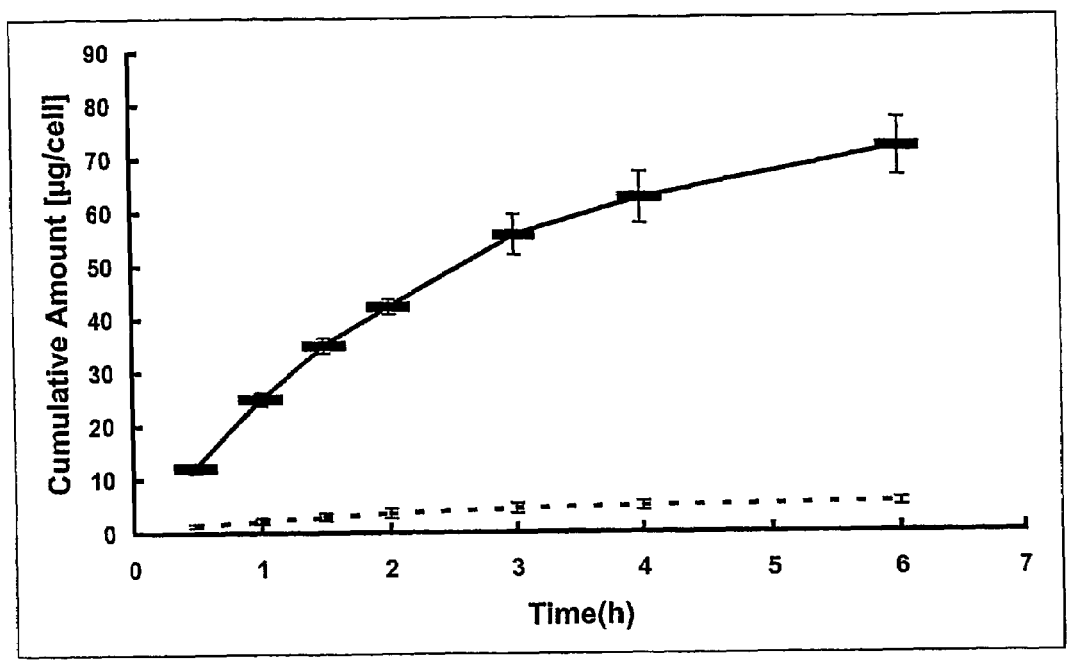

FIG. 4 shows a significant difference in the diffusion rate through the hydrophobic membrane of the two formulations. After 6 hours, 72 μg reach the receptor cell, corresponding to 12.5% of the applied amount (solid line).

In contrast, in the formulation containing Eusolex® UV-Pearls™ OMC, only 5.5 μg reach the receptor phase. This means that 98.94% of the applied UV filter remains on top of the membrane after 6 hours and showed no significant penetration. However, very small quantities may have passed the membrane since the pore size is 200 nm and we have also observed UV-Pearls™ with that small size with e.g. TEM.

Conclusion

Compared to free UV filters, Eusolex® UV-Pearls™ significantly reduce the diffusion of UV filters through a membrane that serves as a model for human skin. Encapsulated UV filters remain on top of the membrane.

Example 4

Epidermal Uptake of UV Filters by Human Epidermis

The goal of this study is to determine and compare both the release of OMC from two different formulations through human epidermal membranes and the epidermal uptake of OMC.

Method

Human female abdominal skin is used to heat-separate the epidermis from the dermis. The epidermal membranes thus obtained are mounted onto a Franz diffusion cell. The receptor cell contains PBS and 4% (w/v) bovine serum albumin, resulting in a pH of 7.4. The temperature is set to 35° C. Each of the two formulations is applied to 3 cells, non-occluded, with a finite dose concentration of 5 mg/cm² (572 μg OMC/cell). The formulations (see Table 3) contain either 8.8% free OMC or 8.8% OMC encapsulated in Eusolex® UV-Pearls™. The duration of examination is 6 hours, 200 μl of the receptor phase is removed at specific points of time and analyzed by HPLC. To analyze the epidermal uptake, the remaining formulation is wiped from the surface of the epidermis with alcohol-soaked tissue and the skin is stripped once with adhesive tape, which is then discarded. A circular punch is used to remove a constant area of epidermis exposed to the formulations. After extraction, OMC concentrations are analyzed by HPLC.

Results

Both formulations, one with free formulated OMC, the other with UV-Pearls™, show no significant amount of UV filter penetrating the epidermis.

Regarding the epidermal uptake or substantivity to the epidermal layers, significant differences between the encapsulated and free OMC are observed (FIG. 5): 3.3 μg of free formulated OMC is collected per mg of epidermal tissue, while only one third of this was found (1.1. μg/mg tissue) if the OMC is encapsulated in Eusolex® UV-Pearls™.

Compared to free UV filters, Eusolex® UV-Pearls™ significantly reduce the uptake of UV filters by heat-separated human epidermis. Free OMC is absorbed by the epidermis 3-fold compared to Eusolex® UV-Pearls™.

Example 5

Sun Protection Spray-Mousse

| | supplier | % by weight |
|---|---|---|
| PHASE A | | |
| Water, Titanium dioxide, Alumina, sodium metaphosphate, phenoxyethanol, sodium methyl paraben (Eusolex ™ T aqua) | 1 | 16.5 |
| PHASE B | | |
| Phenyl benzimidazole Sulfonic Acid (Eusolex ™ 232) | 1 | 3 |
| Sodium hydroxyde | 1 | 0.44 |
| Water | | 10 |
| PHASE C | | |
| Cl 77891 (Titanium dioxide), Mica, Silica (Timiron ™ Splendid gold) | 1 | 1 |
| Sodium Lauroyl OAT Aminoacids (Proteol ™ oat) | 2 | 5 |
| Dimethicone Copolyol Phosphate (Pecosil ™ PS 100) | 2 | 0.5 |
| Disodium EDTA | 1 | 0.1 |
| Chlorphenesin | 1 | 0.3 |
| Glycerol | 1 | 3 |
| Water, demineralized | | Qsp 100 |
| PHASE D | | |
| silica capsules OMC Octylmethoxycinnamate: 42% | 1 | 23 |

Procedure:

Phase A is dispersed in the Phase C. Then phase B and phase D are added and neutralized at pH=8.

Suppliers: 1 Merck
  2 Seppic

Example 6

Sun Protection Spray-mousse

| | supplier | % by weight |
|---|---|---|
| PHASE A | | |
| Water, Titanium dioxide, Alumina, sodium metaphosphate, phenoxyethanol, sodium methyl paraben (Eusolex ™ T aqua) | 1 | 16 |
| PHASE B | | |
| Sodium Lauroyl OAT Aminoacids (Proteol ™ oat) | 2 | 5 |
| Disodium EDTA | 1 | 0.1 |
| Chlorphenesin | 1 | 0.3 |
| Glycerol | 1 | 3 |
| Water, demineralized | | Qsp 100 |
| PHASE C | | |
| silica capsules OMC (Octylmethoxycinnamate: 42%) | 1 | 23 |

Phase B is dispersed in the Phase A. Then phase C is added and neutralized at pH=5,5. (Suppliers: 1: Merck, 2: Seppic)

Example 7

Sun Protection Spray-mousse

| | supplier | % by weight |
|---|---|---|
| PHASE A | | |
| Water, Titanium dioxide, Alumina, sodium metaphosphate, phenoxyethanol, sodium methyl paraben (Eusolex ™ T aqua) | 1 | 16.5 |
| PHASE B | | |
| Phenyl benzimidazole Sulfonic Acid (Eusolex ™ 232) | 1 | 3 |
| Sodium hydroxyde | 1 | 0.44 |
| Water | | 10 |
| PHASE C | | |
| Sodium Lauroyl OAT Aminoacids (Proteol ™ oat) | 2 | 5 |
| Disodium EDTA | 1 | 0.1 |
| Chlorphenesin | 1 | 0.3 |
| Glycerol | 1 | 3 |
| Water, demineralized | | Qsp 100 |
| PHASE D | | |
| silica capsules OMC (Octylmethoxycinnamate: 42%) | 1 | 23 |

Procedure:

Phase A is dispersed in the Phase C. Then phase B and phase D are added and neutralized at pH=8.

Suppliers: 1 Merck
  2 Seppic

The average SPC (3 measurements), measured for a layer of 2 mg/cm$^2$ on Transpore™ Tape (trademark of 3M) 20 min after application, is 22,4.

Example 8

| Eusolex ™ T aqua | 16.5 |
|---|---|
| Eusolex ™ 232 | 3 |
| Eusolex ™ 9020 in silica capsule | 23 |
| Sodium hydroxyde | 0.44 |
| Proteol ™ oat | 5 |
| Disodium EDTA | 0.1 |
| Chlorphenesin1 | 0.3 |
| Glycerol | 3 |
| Water, demineralized | Qsp 100 |

Example 9

| Eusolex ™ T aqua | 16.5 |
|---|---|
| Eusolex ™ 232 | 3 |
| Eusolex ™ 6300 in silica capsule | 20 |
| Sodium hydroxyde | 0.44 |
| Proteol ™ oat | 5 |
| Disodium EDTA | 0.1 |
| Chlorphenesin1 | 0.3 |
| Glycerol | 3 |
| Water, demineralized | Qsp 100 |

Example 10

| | |
|---|---|
| Eusolex ™ T aqua | 16.5 |
| Eusolex ™ 232 | 3 |
| Eusolex ™ OCR in silica capsule | 12 |
| Eusolex ™ 9020 in silica capsule | 12 |
| Sodium hydroxyde | 0.44 |
| Proteol ™ oat | 5 |
| Disodium EDTA | 0.1 |
| Chlorphenesin1 | 0.3 |
| Glycerol | 3 |
| Water, demineralized | Qsp 100 |

Example 11

| | |
|---|---|
| Eusolex ™ T aqua | 16.5 |
| Eusolex ™ 232 | 3 |
| Eusolex ™ 9020/OCR in silica capsule | 12 |
| Eusolex ™ 6300 in silica capsule | 12 |
| Sodium hydroxyde | 0.44 |
| Proteol ™ oat | 5 |
| Disodium EDTA | 0.1 |
| Chlorphenesin1 | 0.3 |
| Glycerol | 3 |
| Water, demineralized | Qsp 100 |

Example 12

| | |
|---|---|
| Eusolex ™ T-2000 | 12 |
| Eusolex ™ 232 | 3 |
| Eusolex ™ 9020 in silica capsule | 12 |
| Sodium hydroxyde | 0.44 |
| Proteol ™ oat | 5 |
| Disodium EDTA | 0.1 |
| Chlorphenesin1 | 0.3 |
| Glycerol | 3 |
| Water, demineralized | Qsp 100 |

TABLE 4

Water-in-oil sunscreen emulsions—values in % (weight/weight)

| | 4-1 | 4-2 | 4-3 | 4-4 | 4-5 | 4-6 | 4-7 | 4-8 | 4-9 | 4-10 |
|---|---|---|---|---|---|---|---|---|---|---|
| Titanium dioxide | | 2 | 5 | | | | | | | 3 |
| Benzylidene malonate polysiloxane | | | | 1 | 2 | | | | 1 | 1 |
| Methylene Bis-Benztriazolyl Tetramethylbutylphenol | | | | | | 1 | 2 | 1 | | |
| Zinc oxide | | | | | | | | 5 | 2 | |
| UV-Pearl, OMC | 30 | 15 | 15 | 15 | 15 | 15 | 15 | 15 | 15 | 15 |
| Polyglyceryl-3-Dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Water | ad 100 | ad 100 | ad 100 | ad 100 | ad 100 | ad 100 | ad 100 | ad 100 | ad 100 | ad 100 |

| | 4-11 | 4-12 | 4-13 | 4-14 | 4-15 | 4-16 | 4-17 | 4-18 |
|---|---|---|---|---|---|---|---|---|
| Titanium dioxide | 3 | | 2 | | | | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| Zinc oxide | | | | 2 | | | | |
| UV-Pearl, OMC | 15 | 15 | 15 | 30 | 30 | 30 | 15 | 15 |
| Polyglyceryl-3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |

TABLE 4-continued

Water-in-oil sunscreen emulsions—values in % (weight/weight)

| | | | | | | | | |
|---|---|---|---|---|---|---|---|---|
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Dicocoyl Pentyerythrityl Citrate (and) Sorbitan Sesquioleate (and) Cera Alba (and) Aluminium Stearate | | | | | 6 | 6 | 6 | 6 |
| PEG-7 Hydrogenated Castor Oil | | | | | 1 | 1 | 1 | 1 |
| Zinc Stearate | | | | | 2 | 2 | 2 | 2 |
| Oleyl Erucate | | | | | 6 | 6 | 6 | 6 |
| Decyl Oleate | | | | | 6 | 6 | 6 | 6 |
| Dimethicone | | | | | 5 | 5 | 5 | 5 |
| Tromethamine | | | | | 1 | 1 | 1 | 1 |
| Glycerin | | | | | 5 | 5 | 5 | 5 |
| Allantoin | | | | | 0.2 | 0.2 | 0.2 | 0.2 |
| water | ad 100 | ad 100 | ad 100 | ad 100 | ad 100 | ad 100 | ad 100 | ad 100 |

| | 4-19 | 4-20 | 4-21 | 4-22 | 4-23 | 4-24 | 4-25 | 4-26 | 4-27 | 4-28 |
|---|---|---|---|---|---|---|---|---|---|---|
| Titanium dioxide | | | | | | 3 | 3 | | 2 | |
| Benzylidene malonate polysiloxane | 1 | 2 | | | 1 | 1 | | 1 | 0.5 | |
| Methylene Bis-Benztriazolyl Tetramethylbutylphenol | | | 2 | 1 | | | 1 | 1 | 0.5 | |
| Zinc oxide | | | | 5 | 2 | | | | 2 | |
| UV-Pearl, OMC | 15 | 15 | 15 | 15 | 15 | 15 | 15 | 15 | 15 | 10 |
| UV-Pearl, OCR | | | | | | | | | | 10 |
| UV-Pearl, OCR, BMDBM | | | | | | | | | | 10 |
| Polyglyceryl-3-Dimerate | | | | | | | | | | 3 |
| Cera Alba | 2 | 2 | 2 | 2 | 2 | 2 | 2 | 2 | 2 | 0.3 |
| Hydrogenated Castor Oil | | | | | | | | | | 0.2 |
| Paraffinium Liquidum | | | | | | | | | | 7 |
| Caprylic/Capric Triglyceride | | | | | | | | | | 7 |
| Hexyl Laurate | | | | | | | | | | 4 |
| PVP/Eicosene Copolymer | | | | | | | | | | 2 |
| Propylene Glycol | | | | | | | | | | 4 |
| Magnesium Sulfate | | | | | | | | | | 0.6 |
| Tocopherol | | | | | | | | | | 0.5 |
| Tocopheryl Acetate | 1 | 1 | 1 | 1 | 1 | 1 | 1 | 1 | 1 | 0.5 |
| Cyclomethicone | | | | | | | | | | 0.5 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Dicocoyl Pentyerythrityl Citrate, Sorbitan Sesquioleate, Cera Alba, Aluminium Stearate | 6 | 6 | 6 | 6 | 6 | 6 | 6 | 6 | 6 | |
| PEG-7 Hydrogenated Castor Oil | 1 | 1 | 1 | 1 | 1 | 1 | 1 | 1 | 1 | |
| Zinc Stearate | 2 | 2 | 2 | 2 | 2 | 2 | 2 | 2 | 2 | |
| Oleyl Erucate | 6 | 6 | 6 | 6 | 6 | 6 | 6 | 6 | 6 | |
| Decyl Oleate | 6 | 6 | 6 | 6 | 6 | 6 | 6 | 6 | 6 | |
| Dimethicone | 5 | 5 | 5 | 5 | 5 | 5 | 5 | 5 | 5 | |
| Tromethamine | 1 | 1 | 1 | 1 | 1 | 1 | 1 | 1 | 1 | |
| Glycerin | 5 | 5 | 5 | 5 | 5 | 5 | 5 | 5 | 5 | |
| Allantoin | 0.2 | 0.2 | 0.2 | 0.2 | 0.2 | 0.2 | 0.2 | 0.2 | 0.2 | |
| Water | | | | | ad 100 | | | | | |

| | 4-29 | 4-30 | 4-31 | 4-32 | 4-33 | 4-34 | 4-35 | 4-36 |
|---|---|---|---|---|---|---|---|---|
| Titanium dioxide | 2 | 5 | | | | | | |
| Benzylidene malonate polysiloxane | | | 1 | 2 | | | | 1 |
| Methylene Bis-Benztriazolyl Tetramethylbutylphenol | | | | | 1 | 2 | 1 | |
| Zinc oxide | | | | | | | 5 | 2 |
| UV-Pearl OMC | 10 | 5 | | 5 | | | | |
| UV-Pearl, Ethylhexyl Dimethyl PABA | 5 | | | | | | | |
| UV-Pearl, Homosalate | | 10 | | | | | | |
| UV-Pearl, OCR, BP-3 | | | 15 | | | | | |
| UV-Pearl, Ethylhexyl Dimethyl PABA, BP-3 | | | | 10 | | | | |
| UV-Pearl, Homosalate, BP-3 | | | | | 15 | | | |
| UV-Pearl, Ethylhexyl salicylate, BP-3 | | | | | | 15 | | |
| UV-Pearl OMC, BMDBM | | | | | | | 15 | |
| UV-Pearl, Ethylhexyl Dimethyl PABA, BMDBM | | | | | | | | 15 |
| Polyglyceryl-3-Dimerate | 3 | 3 | 3 | 3 | 3 | 3 | 3 | 3 |
| Cera Alba | 0.3 | 0.3 | 0.3 | 0.3 | 0.3 | 0.3 | 0.3 | 0.3 |

TABLE 4-continued

Water-in-oil sunscreen emulsions—values in % (weight/weight)

| | | | | | | | | |
|---|---|---|---|---|---|---|---|---|
| Hydrogenated Castor Oil | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 |
| Caprylic/Capric Triglyceride | 7 | 7 | 7 | 7 | 7 | 7 | 7 | 7 |
| Hexyl Laurate | 4 | 4 | 4 | 4 | 4 | 4 | 4 | 4 |
| PVP/Eicosene Copolymer | 2 | 2 | 2 | 2 | 2 | 2 | 2 | 2 |
| Propylene Glycol | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Water | | | | ad 100 | | | | |

| | 4-38 | 4-39 | 4-40 | 4-41 | 4-42 | 4-43 | 4-44 | 4-45 | 4-46 | 4-47 | 4-48 |
|---|---|---|---|---|---|---|---|---|---|---|---|
| Titanium dioxide | | 2 | 5 | | | | | | | 3 | 3 |
| Benzylidene malonate polysiloxane | | | | 1 | | | | | 1 | 1 | |
| Methylene Bis-Benztriazolyl Tetramethylbutylphenol | | | | | 1 | 2 | 1 | | | | 1 |
| Zinc oxide | | | | | | | | 5 | 2 | | |
| UV-Pearl OMC | 5 | 5 | 5 | 5 | 7 | 5 | 5 | 5 | 5 | 5 | 8 |
| UV-Pearl, OCR | | 10 | | | | | | | | | 5 |
| UV-Pearl, Ethylhexyl Dimethyl PABA | | | 10 | | | | | | | | |
| UV-Pearl, Homosalate | | | | 10 | | | | | | | |
| UV-Pearl, Ethylhexyl salicylate | | | | | 10 | | | | | | |
| UV-Pearl, OMC, BP-3 | | | | | | 10 | | | | | |
| UV-Pearl, OCR, BP-3 | | | | | | | 10 | | | | |
| UV-Pearl, Ethylhexyl Dimethyl PABA, BP-3 | | | | | | | | 10 | | | |
| UV-Pearl, Homosalate, BP-3 | | | | | | | | | 10 | | |
| UV-Pearl, Ethylhexyl salicylate, BP-3 | | | | | | | | | | 10 | |
| BMDBM | | | | | | | | | | | 2 |
| UV-Pearl OMC, 4-Methylbenzylidene Camphor | 25 | | | | | | | | | | |
| Polyglyceryl-3-Dimerate | 3 | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 | 0.5 |
| Propylparabene | 0.05 | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 | 0.15 |
| Water | | | | | | ad 100 | | | | | |

| | 4-49 | 4-50 | 4-51 | 4-52 | 4-53 | 4-54 | 4-55 |
|---|---|---|---|---|---|---|---|
| Titanium dioxide | | 2 | 5 | | | 2 | 5 |
| Benzylidene malonate polysiloxane | | 0.5 | | | | | |
| Methylene Bis-Benztriazolyl Tetramethylbutylphenol | | 1 | | | | | |
| Zinc oxide | | | 2 | | | | |
| UV-Pearl, OMC | | 14 | | 5 | 5 | | |
| UV-Pearl, OCR | | | 13 | 5 | 5 | | |
| UV-Pearl, Ethylhexyl salicylate, BP-3 | | | | | | | 15 |
| BMDBM | 3 | 2 | | | | | |
| UV-Pearl, OMC, BMDBM | | | | | | 15 | |
| UV-Pearl, OCR, BMDBM | | | | 15 | 15 | 30 | |
| UV-Pearl, OMC, 4-Methylbenzylidene Camphor | | | | | 5 | | |
| 4-Methylbenziliden Camphor, | | | 3 | | | | |
| Polyglyceryl-3-Dimerate | 3 | 3 | 3 | | | | |
| Cera Alba | 0.3 | 0.3 | 0.3 | 2 | 2 | 2 | 2 |
| Hydrogenated Castor Oil | 0.2 | 0.2 | 0.2 | | | | |
| Paraffinium Liquidum | 7 | 7 | 7 | | | | |
| Caprylic/Capric Triglyceride | 7 | 7 | 7 | | | | |
| Hexyl Laurate | 4 | 4 | 4 | | | | |
| PVP/Eicosene Copolymer | 2 | 2 | 2 | | | | |
| Propylene Glycol | 4 | 4 | 4 | | | | |
| Magnesium Sulfate | 0.6 | 0.6 | 0.6 | | | | |

TABLE 4-continued

| Water-in-oil sunscreen emulsions—values in % (weight/weight) | | | | | | | |
|---|---|---|---|---|---|---|---|
| Tocopherol | 0.5 | 0.5 | 0.5 | | | | |
| Tocopheryl Acetate | 0.5 | 0.5 | 0.5 | 1 | 1 | 1 | 1 |
| Cyclomethicone | 0.5 | 0.5 | 0.5 | | | | |
| Propylparabene | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 |
| Dicocoyl Pentyerythrityl Citrate, Sorbitan Sesquioleate, Cera Alba, Aluminium Stearate | | | | 6 | 6 | 6 | 6 |
| PEG-7 Hydrogenated Castor Oil | | | | 1 | 1 | 1 | 1 |
| Zinc Stearate | | | | 2 | 2 | 2 | 2 |
| Oleyl Erucate | | | | 6 | 6 | 6 | 6 |
| Decyl Oleate | | | | 6 | 6 | 6 | 6 |
| Dimethicone | | | | 5 | 5 | 5 | 5 |
| Tromethamine | | | | 1 | 1 | 1 | 1 |
| Glycerin | | | | 5 | 5 | 5 | 5 |
| Allantoin | | | | 0.2 | 0.2 | 0.2 | 0.2 |
| Water | | | | ad 100 | | | |

TABLE 5

| Oil-in-water sunscreen emulsions, values in % (weight/weight) | | | | | | | | | | |
|---|---|---|---|---|---|---|---|---|---|---|
| | 5-1 | 5-2 | 5-3 | 5-4 | 5-5 | 5-6 | 5-7 | 5-8 | 5-9 | 5-10 |
| Titanium dioxide | | 2 | 5 | | | | | | | 3 |
| Benzylidene malonate polysiloxane | | | | 1 | 2 | | | | 1 | 1 |
| Methylene Bis-Benztriazolyl Tetramethylbutylphenol | | | | | | 1 | 2 | 1 | | |
| Zinc oxide | | | | | | | | | 5 | 2 |
| UV-Pearl, OMC | 30 | 15 | 15 | 15 | 15 | 15 | 15 | 15 | 15 | 15 |
| 4-Methylbenzyliden Camphor | | | | | | | | | | |
| BMDBM | | | | | | | | | | |
| Phenylbenzimidazole Sulfonic Acid | | | 4 | | | | | | | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE | | | | | | | | | | |
| Stearic Acid | | | | | | | | | | |
| Persea Gratissima | | | | | | | | | | |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Tromethamine | | | 1.8 | | | | | | | |
| Glycerin | | | | | | | | | | |
| Water | ad 100 | ad 100 | ad 100 | ad 100 | ad 100 | ad 100 | ad 100 | ad 100 | ad 100 | ad 100 |
| | 5-11 | 5-12 | 5-13 | 5-14 | 5-15 | 5-16 | 5-17 | 5-18 | | |
| Titanium dioxide | 3 | | 2 | | | | 2 | 5 | | |
| Benzylidene malonate polysiloxane | | 1 | 0.5 | | | | | | | |
| Methylene Bis-Benztriazolyl Tetramethylbutylphenol | 1 | 1 | 0.5 | | | | | | | |
| Zinc oxide | | | 2 | | | | | | | |
| UV-Pearl, OMC | 15 | 15 | 15 | 30 | 30 | 30 | 15 | 15 | | |
| 4-Methylbenzyliden Camphor | | | | 3 | | | | | | |
| BMDBM | | | | 1 | | | | | | |
| Phenylbenzimidazole Sulfonic Acid | | | | | 4 | | | | | |
| Stearyl Alcohol (and) Steareth-7 (and) Steareth-10 | 3 | 3 | 3 | 3 | | | | | | |
| Glyceryl Stearate (and) Ceteth-20 | 3 | 3 | 3 | 3 | | | | | | |
| Glyceryl Stearate | 3 | 3 | 3 | 3 | | | | | | |
| Microwax | 1 | 1 | 1 | 1 | | | | | | |
| Cetearyl Octanoate | 11.5 | 11.5 | 11.5 | 11.5 | | | | | | |
| Caprylic/Capric Triglyceride | 6 | 6 | 6 | 6 | 14 | 14 | 14 | 14 | | |
| Oleyl Oleate | 6 | 6 | 6 | 6 | | | | | | |
| Propylene Glycol | 4 | 4 | 4 | 4 | | | | | | |
| Glyceryl Stearate SE | | | | | 6 | 6 | 6 | 6 | | |
| Stearic Acid | | | | | 2 | 2 | 2 | 2 | | |
| Persea Gratissima | | | | | 8 | 8 | 8 | 8 | | |

TABLE 5-continued

Oil-in-water sunscreen emulsions, values in % (weight/weight)

| | | | | | | | | |
|---|---|---|---|---|---|---|---|---|
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Tromethamine | | | | | 1.8 | | | |
| Glycerin | | | | | 3 | 3 | 3 | 3 |
| Water | ad 100 | ad 100 | ad 100 | ad 100 | ad 100 | ad 100 | ad 100 | ad 100 |

| | 5-19 | 5-20 | 5-21 | 5-22 | 5-23 | 5-24 | 5-25 | 5-26 | 5-27 | 5-28 |
|---|---|---|---|---|---|---|---|---|---|---|
| Titanium dioxide | | | | | | | 3 | 3 | | 2 |
| Benzylidene malonate polysiloxane | 1 | 2 | | | | 1 | 1 | | 1 | 0.5 |
| Methylene Bis-Benztriazolyl Tetramethylbutylphenol | | | 1 | 2 | 1 | | | 1 | 1 | 0.5 |
| Zinc oxide | | | | | 5 | 2 | | | | 2 |
| UV-Pearl, OMC | 15 | 15 | 15 | 15 | 15 | 15 | 15 | 15 | 15 | 15 |
| Caprylic/Capric Triglyceride | 14 | 14 | 14 | 14 | 14 | 14 | 14 | 14 | 14 | 14 |
| Oleyl Oleate | | | | | | | | | | |
| Propylene Glycol | | | | | | | | | | |
| Glyceryl Stearate SE | 6 | 6 | 6 | 6 | 6 | 6 | 6 | 6 | 6 | 6 |
| Stearic Acid | 2 | 2 | 2 | 2 | 2 | 2 | 2 | 2 | 2 | 2 |
| Persea Gratissima | 8 | 8 | 8 | 8 | 8 | 8 | 8 | 8 | 8 | 8 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Glyceryl Stearate, Ceteareth-20, Ceteareth-10, Cetearyl Alcohol, Cetyl Palmitate | | | | | | | | | | |
| Ceteareth-30 | | | | | | | | | | |
| Dicaprylyl Ether | | | | | | | | | | |
| Hexyldecanol, Hexyldexyllaurate | | | | | | | | | | |
| Cocoglycerides | | | | | | | | | | |
| Tromethamine | | | | | | | | | | |
| Glycerin | 3 | 3 | 3 | 3 | 3 | 3 | 3 | 3 | 3 | 3 |
| Water | ad 100 | ad 100 | ad 100 | ad 100 | ad 100 | ad 100 | ad 100 | ad 100 | ad 100 | ad 100 |

| | 5-29 | 5-30 | 5-31 | 5-32 | 5-33 | 5-34 | 5-35 | 5-36 |
|---|---|---|---|---|---|---|---|---|
| Titanium dioxide | | | | | | | 2 | 5 |
| Benzylidene malonate polysiloxane | | | 1 | | | | | |
| Methylene Bis-Benztriazolyl Tetramethylbutylphenol | | | | 1 | | | | |
| UV-Pearl, OMC | | 15 | 7.5 | 7.5 | 20 | | 30 | 10 | 10 |
| UV-Pearl, OCR | | | | | 10 | 10 | | |
| UV-Pearl, Ethylhexyl salicylate, BP-3 | | | | | | | 5 | |
| UV-Pearl, OMC, BMDBM | | | | | | 20 | | |
| UV-Pearl, OCR, BMDBM | | | | | | | | 5 |
| 4-Methylbenzyliden Camphor | | | | | 3 | | | |
| BMDBM | | | | | 1 | | | |
| Phenylbenzimidazole Sulfonic Acid | 4 | | | | 4 | | | |
| Stearyl Alcohol (and) Steareth-7 (and) Steareth-10 | | | | | 3 | | | |
| Glyceryl Stearate (and) Ceteth-20 | | | | | 3 | | | |
| Glyceryl Stearate | | | | | 3 | | | |
| Microwax | | | | | 1 | | | |
| Cetearyl Octanoate | | | | | 11.5 | | | |
| Caprylic/Capric Triglyceride | | | | | 6 | 14 | 14 | 14 | 14 |
| Oleyl Oleate | | | | | 6 | | | |
| Propylene Glycol | | | | | 4 | | | |
| Glyceryl Stearate SE | | | | | | 6 | 6 | 6 | 6 |
| Stearic Acid | | | | | | 2 | 2 | 2 | 2 |
| Persea Gratissima | | | | | | 8 | 8 | 8 | 8 |
| Propylparabene | | 0.05 | 0.05 | 0.05 | 0.05 | 0.05 | 0.05 | 0.05 | 0.05 |
| Methylparabene | | 0.15 | 0.15 | 0.15 | 0.15 | 0.15 | 0.15 | 0.15 | 0.15 |
| Glyceryl Stearate, Ceteareth-20, Ceteareth-10, Cetearyl Alcohol, Cetyl Palmitate | 8.6 | 8.6 | 8.6 | | | | | |
| Ceteareth-30 | 3.9 | 3.9 | 3.9 | | | | | |
| Dicaprylyl Ether | 7 | 7 | 7 | | | | | |
| Hexyldecanol, Hexyldexyllaurate | 3 | 3 | 3 | | | | | |
| Cocoglycerides | 3 | 3 | 3 | | | | | |
| Tromethamine | 1.8 | | | | 1.8 | | | |
| Glycerin | | | | | 3 | 3 | 3 | 3 |
| Water | | | | ad 100 | | | | |

TABLE 6

| Sunscreen Gels, values in % (weight/weight) | | | | | | | | | | |
|---|---|---|---|---|---|---|---|---|---|---|
| | 6-1 | 6-2 | 6-3 | 6-4 | 6-5 | 6-6 | 6-7 | 6-8 | 6-9 | 6-10 |
| a = aqueuous gel | | | | | | | | | | |
| Titanium dioxide | | 2 | 5 | | | | | | | 3 |
| Benzylidene malonate polysiloxane | | | 1 | 1 | 2 | | | | 1 | 1 |
| Methylene Bis-Benztriazolyl Tetramethylbutylphenol | | 1 | | | | 1 | 2 | 1 | | |
| Zinc oxide | | | | 2 | | | | 5 | 2 | |
| UV-Pearl, Ethylhexyl Mehtoxycinnamat | 30 | 15 | 15 | 15 | 15 | 15 | 15 | 15 | 15 | 15 |
| 4-Methylbenzyliden Camphor | | | | | 2 | | | | | |
| BMDBM | | 1 | | | | | | | | |
| Phenylbenzimidazole Sulfonic Acid | | | 4 | | | | | | | |
| Prunus Dulcis | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13–14 Isoparaffin (and) Laureth-7 | 3 | 3 | 3 | 3 | 3 | 3 | 3 | 3 | 3 | 3 |
| Carbomer | | | | | | | | | | |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Allantoin | | | | | | | | | | |
| Tromethamine | | | 1.8 | | | | | | | |
| Water | ad 100 | ad 100 | ad 100 | ad 100 | ad 100 | ad 100 | ad 100 | ad 100 | ad 100 | ad 100 |

| | 6-11 | 6-12 | 6-13 | 6-14 | 6-15 | 6-16 | 6-17 | 6-18 |
|---|---|---|---|---|---|---|---|---|
| a = aqueuous gel | | | | a | a | a | a | a |
| Titanium dioxide | 3 | | 2 | | | | | |
| Benzylidene malonate polysiloxane | | 1 | 0.5 | 1 | 2 | | | |
| Methylene Bis-Benztriazolyl Tetramethylbutylphenol | 1 | 1 | 0.5 | | | 1 | 2 | 1 |
| Zinc oxide | | | 2 | | | | | |
| UV-Pearl Ethylhexyl Mehtoxycinnamat | 15 | 15 | 15 | 15 | 15 | 15 | 15 | 15 |
| 4-Methylbenzyliden Camphor | | | | | | | | |
| BMDBM | | | | | | | | |
| Phenylbenzimidazole Sulfonic Acid | | | | | | | | |
| Prunus Dulcis | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |
| PEG-8 (and) Tocopherol (and) Ascorbyl Palmitate (and) Ascorbic Acid (and) Citric Acid | 0.05 | 0.05 | 0.05 | | | | | |
| Sorbitol | 4 | 4 | 4 | 5 | 5 | 5 | 5 | 5 |
| Polyacrylamide (and) C13–14 Isoparaffin (and) Laureth-7 | 3 | 3 | 3 | | | | | |
| Carbomer | | | | 1.5 | 1.5 | 1.5 | 1.5 | 1.5 |
| Propylparabene | 0.05 | 0.05 | 0.05 | | | | | |
| Methylparabene | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | ad 100 | ad 100 | ad 100 | ad 100 | ad 100 | ad 100 | ad 100 | ad 100 |

| | 6-19 | 6-20 | 6-21 | 6-22 | 6-23 | 6-24 | 6-25 | 6-26 | 6-27 | 6-28 |
|---|---|---|---|---|---|---|---|---|---|---|
| w = wassrig | a | a | a | a | a | a | a | a | a | a |
| Titanium dioxide | | | | | | | | | | |
| Methylene Bis-Benztriazolyl Tetramethylbutylphenol | | | | | | | | 1 | 2 | 1 |
| Zinc oxide | | | | | | | | | | |
| UV-Pearl, OMC | 30 | 30 | 15 | 15 | 15 | 11 | 12 | 15 | 15 | 15 |
| UV-Pearl, OCR | | | | | | | | | | |
| UV-Pearl, OMC, Methylene Bis-Benztriazolyl Tetramethylbutylphenol | | | | | | | | | | |
| UV-Pearl, Ethylhexyl salicylate, | | | | | | | | | | |

TABLE 6-continued

Sunscreen Gels, values in % (weight/weight)

| | | | | | | | | | | |
|---|---|---|---|---|---|---|---|---|---|---|
| BMDBM | | | | | | | | | | |
| Disodium Phenyl Dibenzimidazole Tetrasulfonate | | | | | | | | | | |
| Phenylbenzimidazole Sulfonic Acid | | 4 | 4 | | | | | | | |
| Prunus Dulcis | | | | | | | | | | |
| Tocopheryl Acetate | | | | | | | | | | |
| Caprylic/Capric Triglyceride | | | | | | | | | | |
| Octyldodecanol | | | | | | | | | | |
| Decyl Oleate | | | | | | | | | | |
| PEG-8 (and) Tocopherol (and) Ascorbyl Palmitate (and) Ascorbic Acid (and) Citric Acid | | | | | | | | | | |
| Sorbitol | 5 | 5 | 5 | 5 | 5 | 5 | 5 | 5 | 5 | 5 |
| Polyacrylamide (and) C13–14 Isoparaffin (and) Laureth-7 | | | | | | | | | | |
| Carbomer | 1.5 | 1.5 | 1.5 | 1.5 | 1.5 | 1.5 | 1.5 | 1.5 | 1.5 | 1.5 |
| Propylparabene | | | | | | | | | | |
| Methylparabene | 0.15 | 0.15 | 0.15 | 0.15 | 0.15 | 0.15 | 0.15 | 0.15 | 0.15 | 0.15 |
| Allantoin | 0.2 | 0.2 | 0.2 | 0.2 | 0.2 | 0.2 | 0.2 | 0.2 | 0.2 | 0.2 |
| Tromethamine | 2.4 | 4.2 | 4.2 | 2.4 | 2.4 | 2.4 | 2.4 | 2.4 | 2.4 | 2.4 |
| Water | ad 100 | ad 100 | ad 100 | ad 100 | ad 100 | ad 100 | ad 100 | ad 100 | ad 100 | ad 100 |

| | 6-29 | 6-30 | 6-31 | 6-32 | 6-33 | 6-34 | 6-35 | 6-36 |
|---|---|---|---|---|---|---|---|---|
| w = wassrig | | | | a | a | a | a | a |
| Titanium dioxide | 3 | | 2 | | 5 | | | |
| Methylene Bis-Benztriazolyl Tetramethylbutylphenol | 1 | 1 | 0.5 | | | 1 | 2 | 1 |
| Zinc oxide | | | 2 | | | | | |
| UV-Pearl, OMC | 15 | 10 | | 10 | 10 | 10 | 15 | 10 |
| UV-Pearl, OCR | | | 10 | | | | | |
| UV-Pearl, OMC, Methylene Bis-Benztriazolyl Tetramethylbutylphenol | | 7 | | 6 | | | | |
| UV-Pearl, Ethylhexyl salicylate, BMDBM | | | 10 | | | | | |
| Disodium Phenyl Dibenzimidazole Tetrasulfonate | | 3 | | | | 3 | | 3 |
| Phenylbenzimidazole Sulfonic Acid | | 2 | | | 2 | 3 | | 3 |
| Prunus Dulcis | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |
| PEG-8 (and) Tocopherol (and) Ascorbyl Palmitate (and) Ascorbic Acid (and) Citric Acid | 0.05 | 0.05 | 0.05 | | | | | |
| Sorbitol | 4 | 4 | 4 | 5 | 5 | 5 | 5 | 5 |
| Polyacrylamide (and) C13–14 Isoparaffin (and) Laureth-7 | 3 | 3 | 3 | | | | | |
| Carbomer | | | | 1.5 | 1.5 | 1.5 | 1.5 | 1.5 |
| Propylparabene | 0.05 | 0.05 | 0.05 | | | | | |
| Methylparabene | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | ad 100 | ad 100 | ad 100 | ad 100 | ad 100 | ad 100 | ad 100 | ad 100 |

| | 6-37 | 6-38 | 6-39 | 6-40 | 6-41 | 6-42 | 6-43 | 6-44 | 6-45 | 6-46 |
|---|---|---|---|---|---|---|---|---|---|---|
| Titanium dioxide | | 2 | 5 | | | | | | | 3 |
| Benzylidene malonate polysiloxane | | | 1 | 1 | 2 | | | | 1 | 1 |
| Methylene Bis-Benztriazolyl Tetramethylbutylphenol | | 1 | | | | 1 | 2 | 1 | | |
| Zinc oxide | | | | 2 | | | | | 5 | 2 |
| UV-Pearl, OMC | 30 | 5 | 5 | 5 | 5 | 5 | 5 | 5 | 5 | 5 |
| UV-Pearl, OCR | | 10 | | | | | | | | |
| UV-Pearl, Ethylhexyl Dimethyl PABA | | | 10 | | | | | | | |
| UV-Pearl, Homosalate | | | | 10 | | | | | | |
| UV-Pearl, Ethylhexyl salicylate | | | | | 10 | | | | | |
| UV-Pearl, OMC, BP-3 | | | | | | 10 | | | | |
| UV-Pearl, OCR, BP-3 | | | | | | | 10 | | | |
| UV-Pearl, Ethylhexyl Dimethyl PABA, BP-3 | | | | | | | | 10 | | |
| UV-Pearl, Homosalate, BP-3 | | | | | | | | | 10 | |

TABLE 6-continued

Sunscreen Gels, values in % (weight/weight)

| | | | | | | | | | | |
|---|---|---|---|---|---|---|---|---|---|---|
| UV-Pearl, Ethylhexyl salicylate, BP-3 | | | | | | | | | | 10 |
| 4-Methylbenzyliden Camphor | | | | 2 | | | | | | |
| BMDBM | | 1 | | | | | | | | |
| Phenylbenzimidazole Sulfonic Acid | | | 4 | | | | | | | |
| Prunus Dulcis | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8, Tocopherol, Ascorbyl Palmitate, Ascorbic Acid, Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13–14 Isoparaffin (and) Laureth-7 | 3 | 3 | 3 | 3 | 3 | 3 | 3 | 3 | 3 | 3 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | | | | | ad 100 | | | | | |

| | 6-47 | 6-48 | 6-49 | 6-50 | 6-51 | 6-52 | 6-53 | 6-54 |
|---|---|---|---|---|---|---|---|---|
| a = aqueous gel | | | | a | a | a | a | a |
| Titanium dioxide | 3 | | 2 | | | | | |
| Benzylidene malonate polysiloxane | | 1 | 0.5 | 1 | 2 | | | |
| Methylene Bis-Benztriazolyl Tetramethylbutylphenol | 1 | 1 | 0.5 | | | 1 | 2 | 1 |
| Zinc oxide | | | 2 | | | | | |
| UV-Pearl, OMC | 5 | 5 | 5 | 5 | 5 | 5 | 5 | 5 |
| UV-Pearl, OCR, BP-3 | | | 5 | | | | | |
| UV-Pearl, OMC, BMDBM | 10 | | | | | | | |
| UV-Pearl, OCR, BMDBM | | 10 | | | | | | |
| UV-Pearl, Homosalate, BMDBM | | | | 10 | | | | |
| UV-Pearl, Ethylhexyl salicylate, BMDBM | | | | | 10 | | | |
| UV-Pearl, OMC, 4-Methylbenzylidene Camphor | | | | | | 10 | | |
| UV-Pearl, OCR, 4-Methylbenzylidene Camphor | | | | | | | 10 | |
| UV-Pearl, Ethylhexyl Dimethyl PABA, 4-Methylbenzylidene Camphor | | | | | | | | 10 |
| UV-Pearl, Ethylhexyl salicylate, 4-Methylbenzylidene Camphor | | | 5 | | | | | |
| Prunus Dulcis | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |
| PEG-8; Tocopherol; Ascorbyl Palmitate; Ascorbic Acid; Citric Acid | 0.05 | 0.05 | 0.05 | | | | | |
| Sorbitol | 4 | 4 | 4 | 5 | 5 | 5 | 5 | 5 |
| Polyacrylamide, $C_{13-14}$ Isoparaffin, Laureth-7 | 3 | 3 | 3 | | | | | |
| Carbomer | | | | 1.5 | 1.5 | 1.5 | 1.5 | 1.5 |
| Propylparabene | 0.05 | 0.05 | 0.05 | | | | | |
| Methylparabene | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | | | | ad 100 | | | | |

LIST OF FIGURES

FIG. 1: Photo-acoustic response. Given as signal in a.u. (arbitrary units) versus time coming from the skin during the in vivo application. Non-encapsulated OMC versus Eusolex® UV-Pearls™ OMC. The upper part represents the monitoring for OMC at a wavelength of 266 nm. Underneath, the behavior of the formulation itself is monitored at 355 nm as a control experiment.

FIG. 2: Distribution profile of Eusolex® UV-Pearls™ OMC in the horny layer of porcine skin after in vitro application. The distance between two horizontal lines represents the amount of stratum corneum (SC) per strip. The SC amount varies from strip to strip but on average it decreases with increasing strip number. The horizontal length of the column represents the concentration of the OMC. 100% of stratum corneum correspond to 20 μm.

Figure 3:
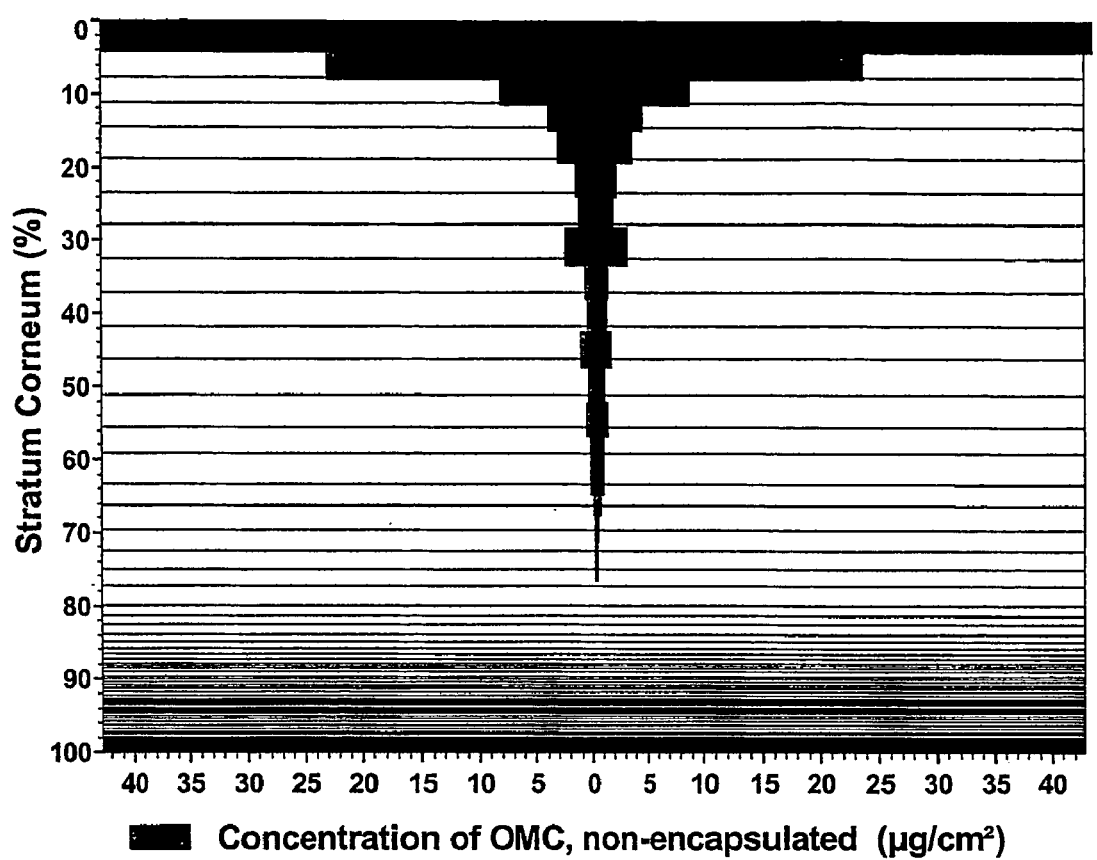

FIG. 3: Distribution profile of free OMC in the horny layer of porcine skin after in vitro application. The distance between two horizontal lines represents the amount of stratum corneum (SC) per strip. The SC amount varies from strip to strip but on average it decreases with increasing strip number. The horizontal length of the column represents the concentration of the OMC. 100% of stratum corneum correspond to 20 μm.

FIG. 4: Comparison of the cumulative release of OMC as a function of time (hrs) during the first 6 hours from each of the two formulations—OMC free formulated (solid line, ■), and Eusolex® UV-Pearls™ OMC (dotted line, - - ) through. Tuffryn® following finite dosing (5 mg/cm$^2$), mean±SD, n=3.

Figure 5:
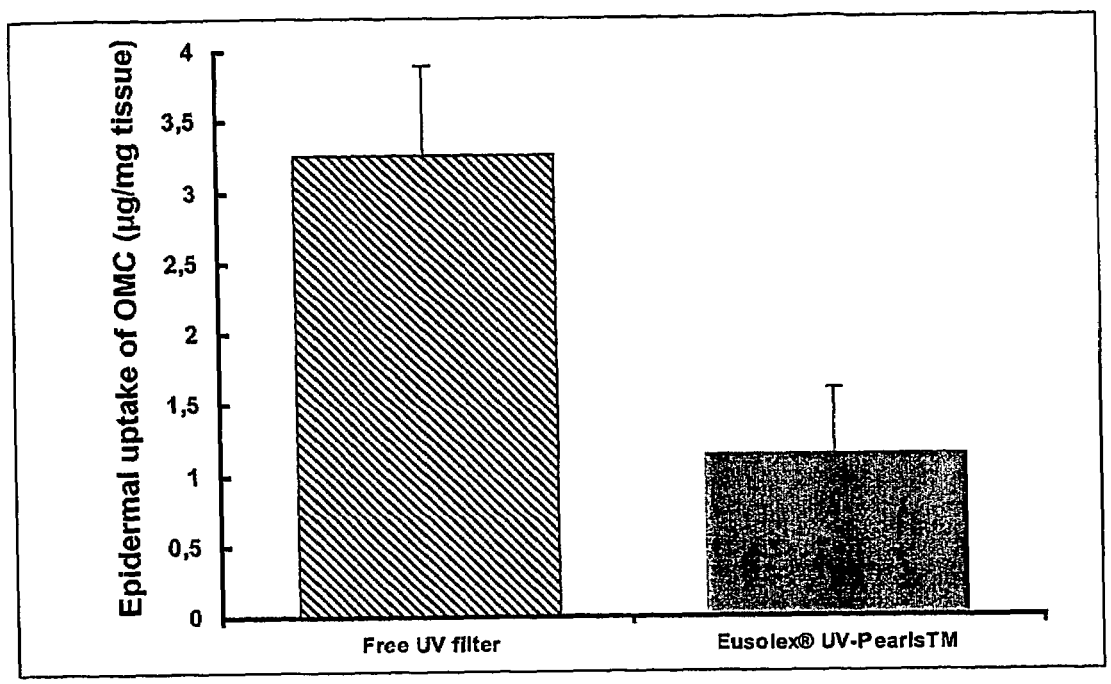

FIG. 5: Epidermal uptake of OMC by epidermal membranes (heat-separated from the dermis) after 6 hours of exposure to each formulation following finite dosing (5 mg/cm$^2$).

The invention claimed is:

1. A composition having UV protection properties comprising
    A) at least one encapsulated organic sunscreen, and
    B) at least one micronized organic UV filter,
wherein the skin penetration capability of the composition is reduced by at least 10% compared to compositions with the same, but unencapsulated, organic sunscreen.

2. A composition according to claim 1, wherein the skin penetration is reduced by at least 20% compared to compositions with the same, but unencapsulated, organic sunscreen.

3. A composition according to claim 1, wherein the at least one encapsulated organic sunscreen is encapsulated in capsules predominantly containing an organic polymeric material and/or inorganic oxidic material.

4. A composition according to claim 1, wherein the capsules have an average particle size in the range of about 10 nm to about 10000 nm.

5. A composition according to claim 1, wherein the composition comprises no organic sunscreen agents in soluble form.

6. A composition according to claim 1, wherein the composition comprises at least one inorganic sunscreen agent.

7. A composition according to claim 1, wherein at least one organic sunscreen is immobilized by being coupled to a surface or a polymeric chain.

8. A composition according to claim 1, which comprises at least one polymeric UV filter.

9. A composition according to claim 1, wherein the at least one micronized organic UV filter is a triazine compound, benzotriazole compound, vinyl group-containing amide compound, cinnamic acid amide compound or sulfonated benzimidazole compound.

10. A composition according to claim 1, which comprises 3-(4'-methylbenzylidene)-dl-camphor, 1-(4-tert-butylphenyl)-3 -(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, or a potassium, sodium or triethanolamine salt thereof, or coated titanium dioxide.

11. A composition according to claim 1, which is a hydrogel.

12. A composition according to claim 1, which is a cosmetic formulation.

13. A composition according to claim 1, which is a pharmaceutical formulation.

14. A method for the prophylaxis of damage to the skin caused by sunrays comprising administering to the skin a composition according to claim 1.

15. A method according to claim 14, wherein the composition is a cosmetic composition.

16. A method for preparing a sunscreen composition according to claim 1, comprising mixing together at least one encapsulated organic sunscreen and at least one micronized organic UV filter.

17. A composition according to claim 1, wherein the capsules have an average particle size in the range of about 10 nm to about 5000 nm.

18. A composition according to claim 1, wherein the composition comprises zinc or titanium dioxide.

19. A composition according to claim 1, wherein at least one organic sunscreen is immobilised by being coupled to a surface of an inorganic sunscreen particle or a siloxane polymeric chain.

20. A method for the prophylaxis of sunburn or sun-caused erythrema of the skin comprising administering to the skin a composition according to claim 1.

* * * * *